United States Patent
Bosanac et al.

(10) Patent No.: US 10,364,255 B2
(45) Date of Patent: Jul. 30, 2019

(54) HETEROAROMATIC COMPOUNDS AS VANIN INHIBITORS

(71) Applicant: Boehringer Ingelheim International GmbH, Ingelheim am Rhein (DE)

(72) Inventors: Todd Bosanac, New Milford, CT (US); Michael J. Burke, Newtown, CT (US); Brian Nicholas Cook, New Milford, CT (US); Darren Todd Disalvo, New Milford, CT (US); Thomas Martin Kirrane, Jr., Middlebury, CT (US); Yue Shen, Ridgefield, CT (US)

(73) Assignee: Boehringer Ingleheim International GmbH, Ingleheim am Rhein (DE)

( * ) Notice: Subject to any disclaimer, the term of this patent is extended or adjusted under 35 U.S.C. 154(b) by 0 days.

(21) Appl. No.: 16/003,252

(22) Filed: Jun. 8, 2018

(65) Prior Publication Data

US 2018/0354968 A1    Dec. 13, 2018

Related U.S. Application Data

(60) Provisional application No. 62/518,106, filed on Jun. 12, 2017.

(51) Int. Cl.
| | | |
|---|---|---|
| *C07D 498/04* | (2006.01) | |
| *C07D 498/10* | (2006.01) | |
| *C07D 519/00* | (2006.01) | |

(52) U.S. Cl.
CPC ......... *C07D 498/04* (2013.01); *C07D 498/10* (2013.01); *C07D 519/00* (2013.01)

(58) Field of Classification Search
CPC ... C07D 498/04; C07D 498/10; C07D 519/00
USPC .................................................... 514/211.11
See application file for complete search history.

(56) References Cited

FOREIGN PATENT DOCUMENTS

| WO | 2005035524 A1 | 4/2005 | |
|---|---|---|---|
| WO | WO-2016193844 A1 * | 12/2016 | ........... C07D 239/28 |
| WO | 2018011681 A1 | 1/2018 | |

OTHER PUBLICATIONS

Berge, Stephen M. et al. "Journal of Pharmaceutical Salts" Jan. 1977, vol. 66, No. 1, 1-19.
Berruyer, C. et al. "Vanin-1-/- Mice Exhibit a Glutathione-Mediated Tissue Resistance to Oxidative Stress" (2004) Molecular and Cellular Biology, vol. 24, No. 16, 7214-7224.
Berruyer, Carole et al. "Vanin-1 licenses inflammatory mediator production by gut epithelial cells and controls colitis by antagonizing peroxisome proliferator-activated receptor y actiivity" (2006) The Journal of Experimental Medicine, vol. 203, No. 13, 2817-2827.
Chai, Chi-Yung et al. "VNN1 overexpression is associated with poor response to preoperative chemoradiotherapy and adverse prognosis in patients with rectal cancers" (2016) American Journal of Translational Research, vol. 8, No. 10, 4455-4463.
Gensollen, Thomas et al. "Functional Polymorphisms in the Regulatory Regions of the VNN1 Gene are Associated with Susceptibility to Inflammatory Bowel Diseases" (2013) Inflammatory Bowel Diseases, vol. 19, No. 1, 2315-2325.
International Search Report PCT/EP2018/065140 dated Jul. 31, 2018.
Jansen, Patrick A.M. et al. "Expression of the Vanin Gene Family in Normal and Inflamed Human Skin: Induction by Proinflammatory Cytokines" (2009) The Journal of Investigative Dermatology, vol. 129, No. 9, 2167-2174.
Kang, Muxing et al "VNN1, a potential biomarker for pancreatic cancer-associated new-onset diabetes, aggravates paraneoplastic islet dysfunction by increasing oxidative stress" (2016) Cancer Letters, 373, 241-250.
Kavian, Niloufar et al. "Imbalance of the Vanin-1 Pathway in Systemic Sclerosis" (2016) The Journal of Immunology, 197, 3326-3335.
Khor, Bernard et al. "Genetics and pathogenesis of inflammatory bowel disease" (2011) Nature, vol. 474, 307-317.
Lipinski, Boguslaw "Pathophysiology of oxidative stress in diabetes mellitus" (2001) Journal of Diabetes and its Complications, vol. 15, 203-210.
Martin, Florent et al. "Vanin genes are clustered (human 6q22-24 and mouse 10A2B1 and encode isoforms of pantetheinase ectoenzymes" (2001) Immunogenetics, 53: 296-306.
Martin, Florent et al. "Vanin-1 -/- mice show decreased NSAID- and Schistosoma-induced intestinal inflammation associated with higher glutathione stores" (2004) The Journal of Clinical Investigation, vol. 113(4) 591-597.
Naquet, Phillippe et al. "Role of the Vnn1 pantetheinase in tissue tolerance to stress" (2014) Biochemical Society Transactions, vol. 42, part 4, 1094-1100.
Pouyet, Laurent et al. "Epithelial vanin-1 controls inflammation-driven carcinogenesis in the colitis-associated colon cancer model" (2010) Inflammatory Bowel Diseases, vol. 16, No. 1, 96-104.
Sosa, Venus et al. "Oxidative stress and cancer: An overview" (2013) Ageing Research Reviews, vol. 12, 376-390.
Zhang, Bing et al. "The role of vanin-1 and oxidative stress-related pathways in idstinguishing acute and chronic pediatric ITP" (2011) Blood, vol. 117, No. 17, 4569-4579.

* cited by examiner

*Primary Examiner* — Kristin A Vajda
(74) *Attorney, Agent, or Firm* — Atabak R. Royace

(57) ABSTRACT

The present invention encompasses compounds of the formula (I)

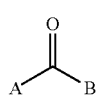

(I)

wherein the groups A and B are defined herein, which are suitable for the treatment of diseases related to Vanin, and processes for making these compounds, pharmaceutical preparations containing these compounds, and their methods of use.

39 Claims, No Drawings

HETEROAROMATIC COMPOUNDS AS VANIN INHIBITORS

BACKGROUND OF THE INVENTION

1. Technical Field

The present invention relates to novel compounds which inhibit Vanin, pharmaceutical compositions containing the same and their use as medicaments.

2. Background Information

Isoforms 1 and 2 of Vanin enzymes are single-domain extracellular pantetheinases that catalyze the cleavage of pantethine and pantetheine into pantothenic acid and cystamine and cysteamine, respectively (Martin, Immunogenetics, (2001 May-June) Vol. 53, No. 4, pp. 296-306). Generation of cysteamine has been linked to increased oxidative in tissue stress resulting from decreased glutathione levels, a condition characteristic of many pathological conditions, including IBD (Xavier, Nature. 2011 Jun. 15; 474 (7351): 307-17), cancer (Sosa, Ageing research reviews, (2013 January) Vol. 12, No. 1, pp. 376-90) and diabetes (Lipinski, Journal of diabetes and its complications, (2001 July-August) Vol. 15, No. 4, pp. 203-10).

Increased Vanin-1 activity in the gut epithelium has been implicated in promoting tissue damage and inflammation by reducing resistance to oxidative stress in murine models (Naquet, Biochem Soc Trans. 2014 August; 42(4):1094-100); (Berruyer, Molecular and cellular biology, (2004 August) Vol. 24, No. 16, pp. 7214-24); (Berruyer, The Journal of experimental medicine, (2006 Dec. 25) Vol. 203, No. 13, pp. 2817-27); (Pouyet, Inflammatory bowel diseases, (2010 January) Vol. 16, No. 1, pp. 96-104). Homozygous VNN1 knock-out (KO) mice lack appreciable levels of cysteamine in blood and tissues and show glutathione-mediated tissue resistance to oxidative stress (Berruyer, The Journal of experimental medicine, (2006 Dec. 25) Vol. 203, No. 13, pp. 2817-27). In addition, these mice are protected from intestinal injury in TNBS, DSS and Schistosoma-induced colitis models (Berruyer, The Journal of experimental medicine, (2006 Dec. 25) Vol. 203, No. 13, pp. 2817-27; Pouyet, Inflammatory bowel diseases, (2010 January) Vol. 16, No. 1, pp. 96-104; Martin, The Journal of clinical investigation, (2004 February) Vol. 113, No. 4, pp. 591-7). Given rodents lack Vanin-2, their only source of cysteamine is from Vanin-1, therefore the protective phenotype of the VNN1 KO mouse is attributed to the lack of cysteamine.

In humans, Vanin-1 was observed to be upregulated in intestinal epithelium in tissue biopsies from UC and CD patients and a functional polymorphism in the regulatory region of the VNN1 gene which led to increased VNN1 expression was associated with increased IBD susceptibility (P=0.0003 heterozygous vs. wild-type) (Gensollen, Inflammatory bowel diseases, (2013 October) Vol. 19, No. 11, pp. 2315-25).

In addition, upregulation of Vanin-1 activity in the skin and blood has been linked to development and severity of fibrosis in Systemic Sclerosis patients (Kavian, Journal of immunology (Baltimore, Md.: 1950), (Oct. 15, 2016) Vol. 197, No. 8, pp. 3326-3335), and elevated levels of Vanin-1 have been observed in chronic Juvenile Idiopathic Thrombocytopenia (Zhang, Blood, (2011 Apr. 28) Vol. 117, No. 17, pp. 4569-79), Psoriasis and Atopic Dermatitis (Jansen, The Journal of investigative dermatology, (2009 September) Vol. 129, No. 9, pp. 2167-74).

Elevated Vanin-1 expression and activity are also present and serve as biomarkers for pancreatic cancer associated new-onset diabetes (Kang, Cancer Letters (New York, N.Y., United States) (2016), 373(2), 241-250) and are also correlated with poor prognosis and response to treatment in colorectal cancer (Chai, American journal of translational research, (2016) Vol. 8, No. 10, pp. 4455-4463).

WO2018011681 discloses Vanin inhibitors for the treatment of a series of diseases e.g. Crohn's disease and ulcerative colitis.

The problem to be solved by the present invention is to provide novel compounds which act as inhibitors of Vanin enzymes, preferably as inhibitors of the Vanin-1 enzyme.

It has been surprisingly found that the compounds of the present invention possess potent Vanin-1 inhibitors activity, preferably exhibiting an inhibition of VNN-1 $IC_{50}$ [nM]<100, particularly preferred $IC_{50}$ [nM]<10.

Moreover the compounds of the present invention exhibit capacities, which are favorable for their pharmacological profile like high solubility and in general desirable pharmacokinetic properties, e.g. metabolic stability.

DETAILED DESCRIPTION OF THE INVENTION

It has surprisingly been found that the problem mentioned above is solved by compounds of formula I of the present invention.

In a first generic embodiment, there is provided a compound of the formula (I)

wherein A is:

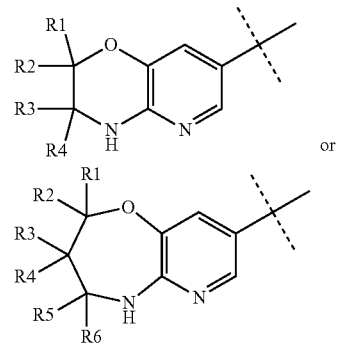 or wherein each R1, R2, R3, R4, R5, and R6 is independently H, $C_{1-4}$-alkyl, or $C_{1-4}$-alkyl substituted with a hydroxyl or halogen group, phenyl, 5-6 membered heteroaryl, or R1 and R2, R3 and R4 or R5 and R6 together form a 3-4 membered carbocycle, and wherein B is:

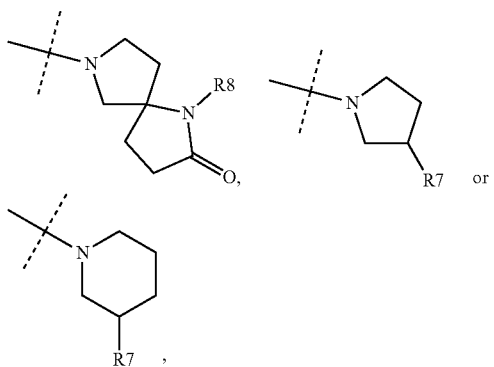 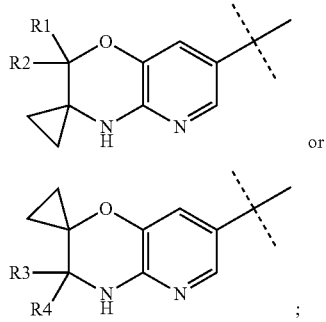

wherein R7 is H, $C_{1-3}$-alkyl, halogen, $C_{1-3}$-alkoxy, 5-6 membered heteroaryl, or

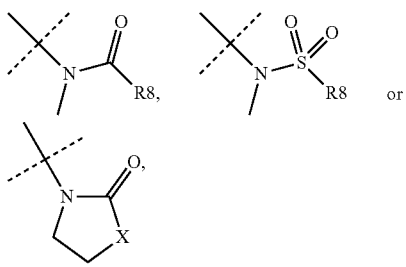

wherein R8 is $C_{1-6}$-alkyl, $C_{3-6}$-cycloalkyl, or heterocycle and X is $CH_2$ or O; or a pharmaceutically acceptable salt or hydrate thereof.

In an aspect relating to the first generic embodiment, there is provided a compound of the formula (I) wherein A is:

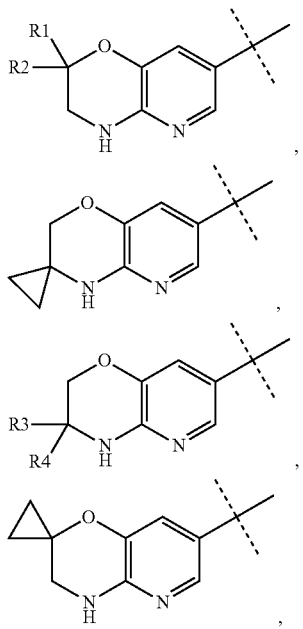

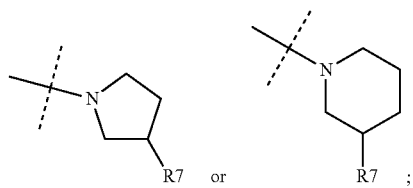

or a pharmaceutically acceptable salt or hydrate thereof.

In another aspect relating to the first generic embodiment, there is provided a compound of the formula (I) wherein B is:

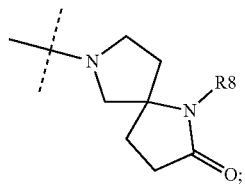

or a pharmaceutically acceptable salt or hydrate thereof.

In another aspect relating to the first generic embodiment, there is provided a compound of the formula (I) wherein B is:

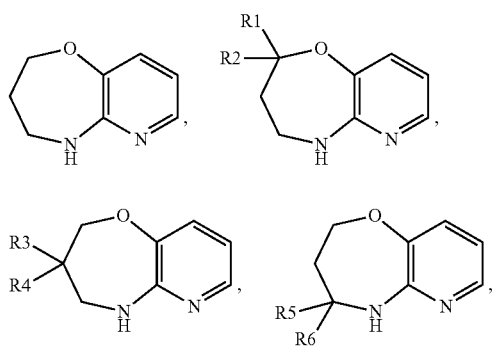

or a pharmaceutically acceptable salt or hydrate thereof.

In another aspect relating to the first generic embodiment, there is provided a compound of the formula (I) wherein A is:

-continued

[Chemical structures with R1, R2, R3, R4 substituents on oxazepine-pyridine fused rings]

or a pharmaceutically acceptable salt or hydrate thereof.

In another aspect relating to the first generic embodiment, there is provided a compound of the formula (I) wherein B is:

[Pyrrolidine and piperidine structures with R7 substituent]

or a pharmaceutically acceptable salt or hydrate thereof.

In another aspect relating to the first generic embodiment, there is provided a compound of the formula (I) wherein B is:

[Spirocyclic pyrrolidine-pyrrolidinone structure with R8 substituent]

or a pharmaceutically acceptable salt or hydrate thereof.

In a second generic embodiment, there is provided a compound chosen from:

[Series of specific chemical structures of pyrido-oxazine compounds with various substituents]

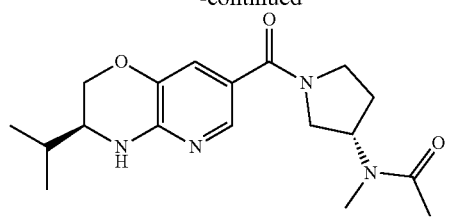
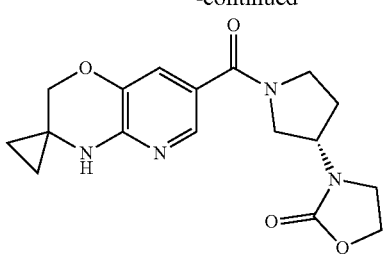
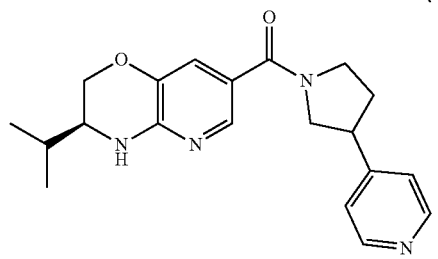
*Ex. 11
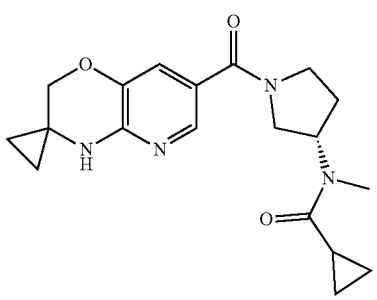
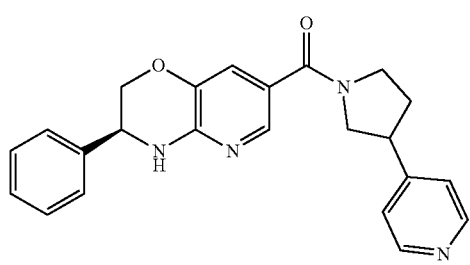
*Ex. 12
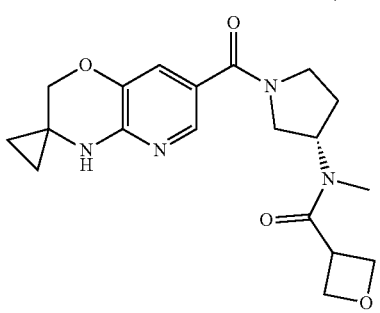
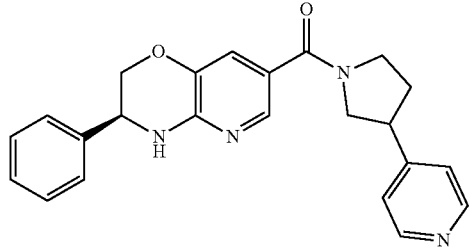
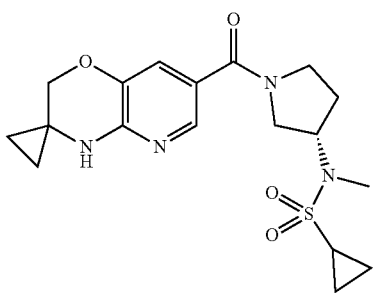
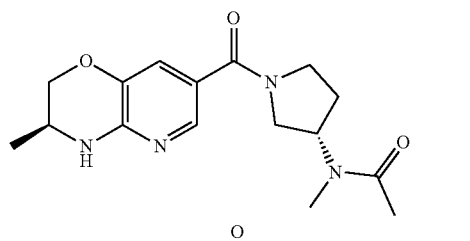
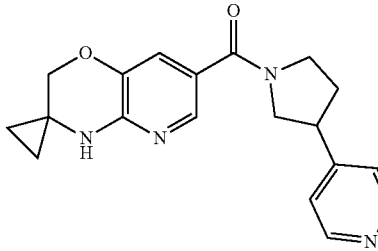
*Ex. 20
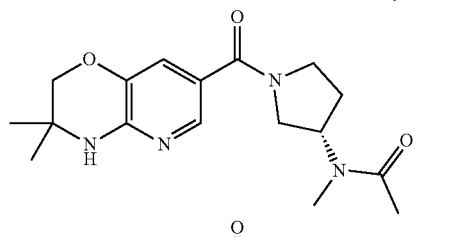
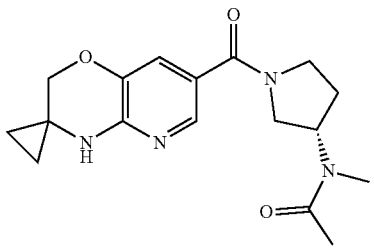
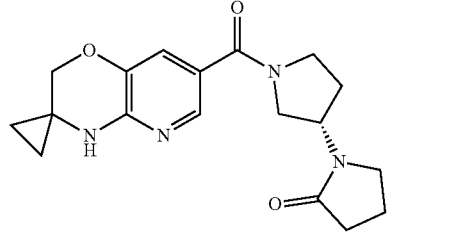

-continued
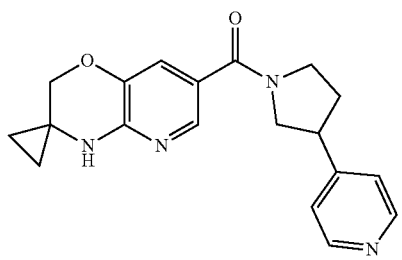
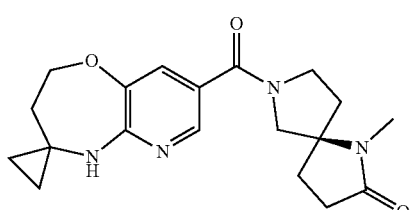
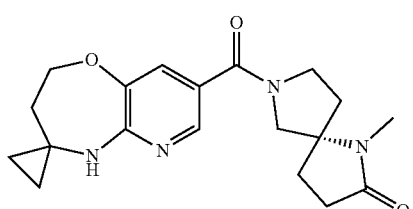
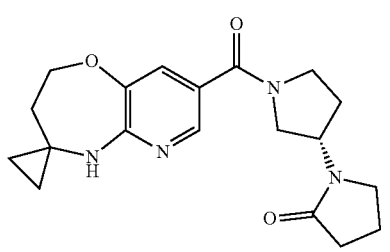
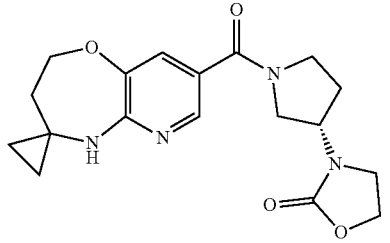
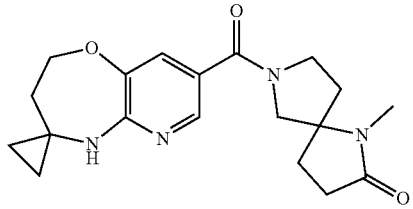
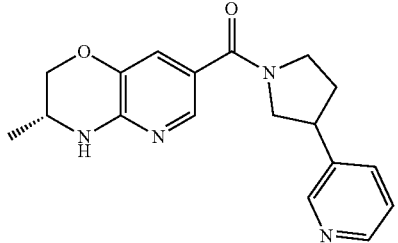
-continued
*Ex. 22
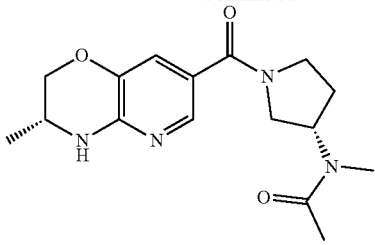
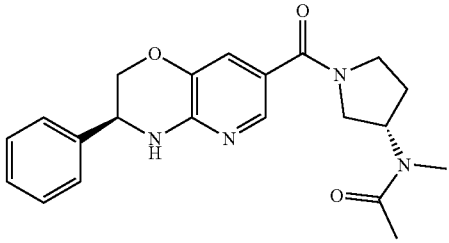
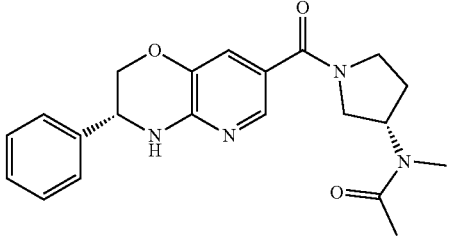
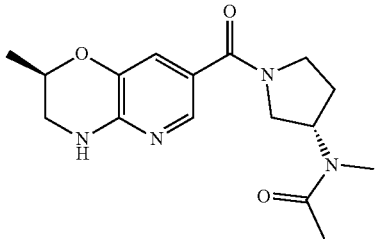
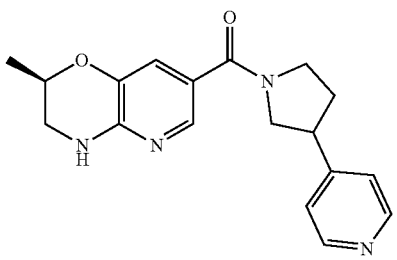
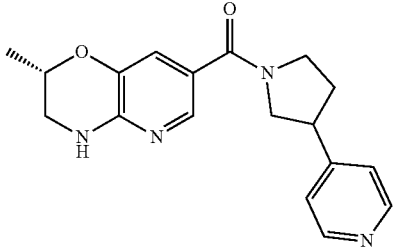
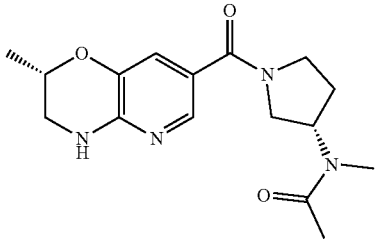

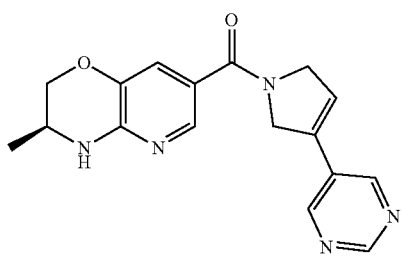
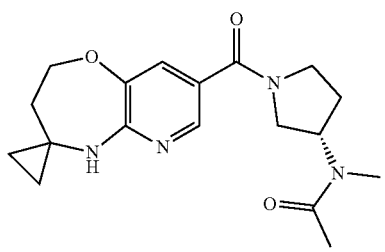
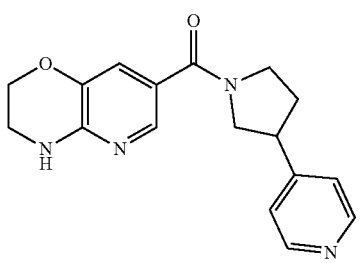
*Ex. 38
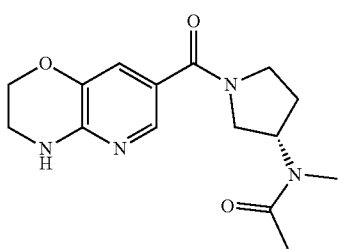
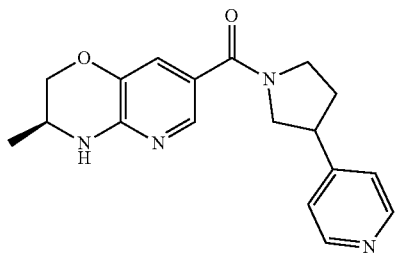
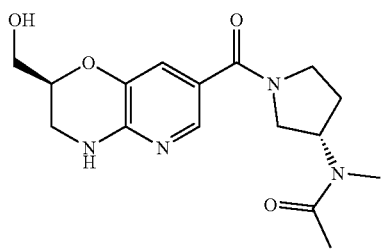
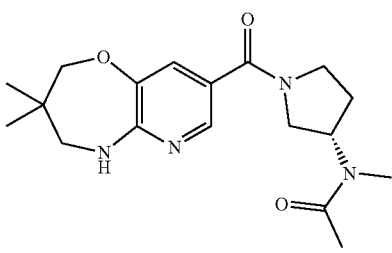
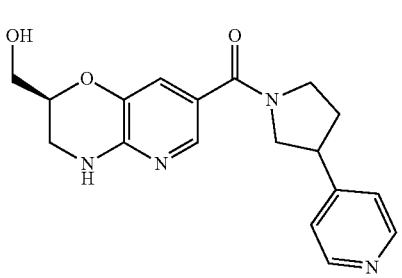
*Ex. 43
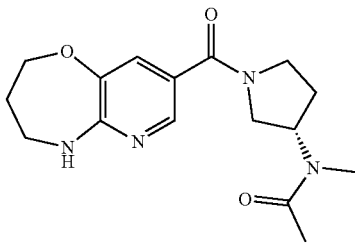
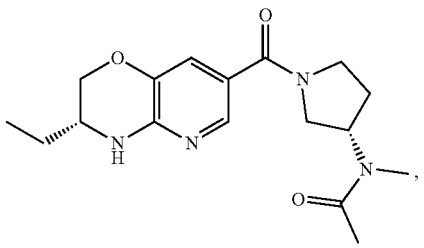
*The stereochemistry at the 3-position of the pyrrolidine-ring of the enantiomerically pure compound was not determined.
or a pharmaceutically acceptable salt or hydrate thereof.
In an aspect relating to the second generic embodiment, the compound is:
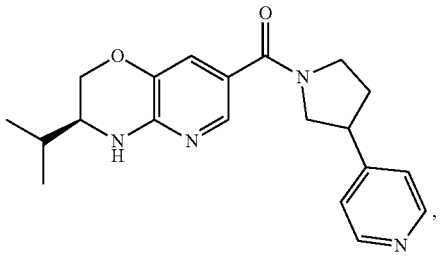

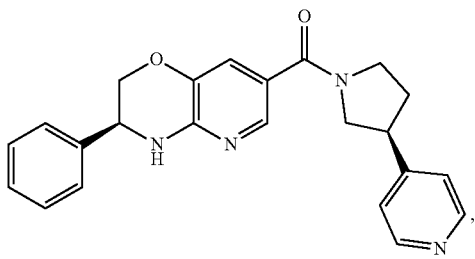

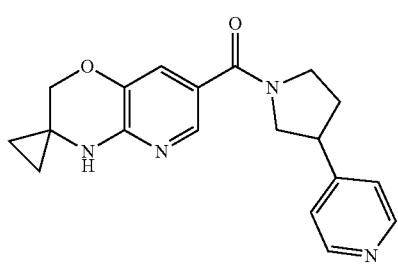

*Ex. 20 and *Ex. 22

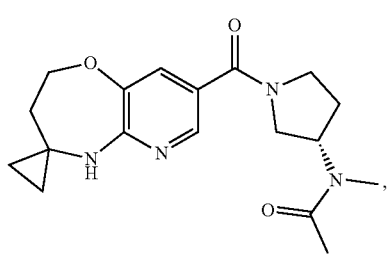

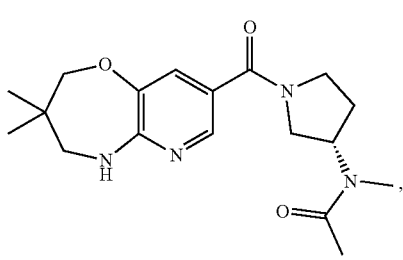

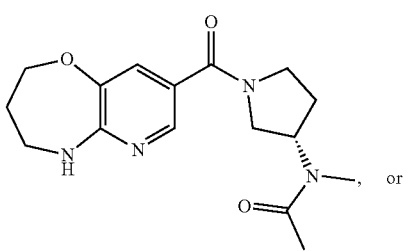

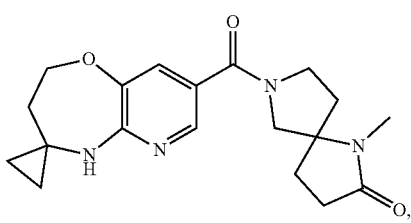

, or

or the pharmaceutically acceptable salt or hydrate thereof.

In a third generic embodiment, there is provided a pharmaceutical composition comprising a therapeutically effective amount of a compound according to the first embodiment or any of its related embodiments or a pharmaceutically acceptable salt thereof.

In a fourth generic embodiment, there is provided a method of treating a disease chosen from Crohn's disease, ulcerative colitis, atopic dermatitis, psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, colorectal cancer and pancreatic cancer related new onset diabetes comprising administering to a patient a therapeutically effective amount of a compound according to the first embodiment or any of its related embodiments or a pharmaceutically acceptable salt thereof.

In a fifth generic embodiment, there is provided a process for preparation of a compound according to the first embodiment or any of its related embodiments by the methods shown herein below The present invention therefore relates to a compound of formula I $$A-\overset{O}{\underset{}{C}}-B \qquad (I)$$

wherein

A is a group of formula A.1 or A.2:

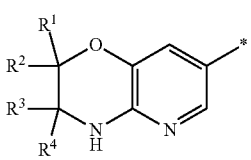

or

A.2
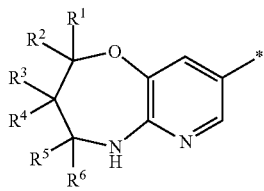

wherein each R¹, R², R³, R⁴, R⁵, and R⁶ is independently selected from the group consisting of H, $C_{1-4}$-alkyl, $C_{1-4}$-alkyl substituted with a hydroxyl or halogen group, phenyl and 5-6 membered heteroaryl, or R¹ and R², R³ and R⁴, or R⁵ and R⁶ together form a 3-4 membered carbocycle, and wherein B is selected from the group consisting of formulas B.1, B.2 and B.3:

B.1
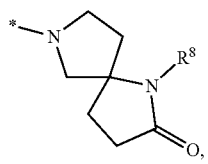

B.2
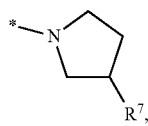

B.3
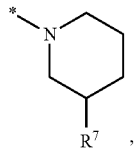

wherein

R⁷ is H, $C_{1-3}$-alkyl, halogen, $C_{1-3}$-alkoxy, 5-6 membered heteroaryl, or R⁷ is selected from the group consisting of $R^{7.a}$, $R^{7.b}$ and $R^{7.c}$ $R^{7.a}$
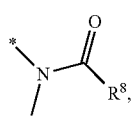

$R^{7.b}$
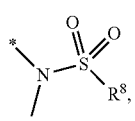

$R^{7.c}$
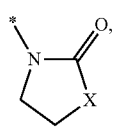

wherein

R⁸ is selected from the group consisting of $C_{1-6}$-alkyl, $C_{3-6}$-cycloalkyl and 3-14 membered heterocyclyl and X is $CH_2$ or O;

or a pharmaceutically acceptable salt thereof.

Preferred Embodiments

In another embodiment of the present invention A denotes a group of formula A.1.

A.1
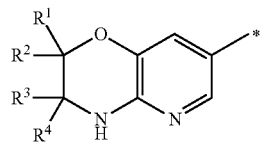

In another embodiment of the present invention
A is selected from the group consisting of formulas A.1a to A.1f A.1a
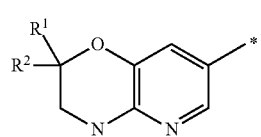

A.1b
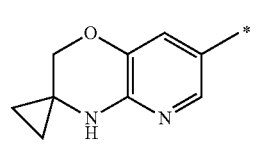

A.1c
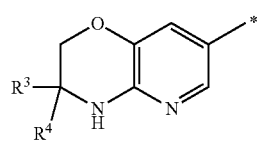

A.1d
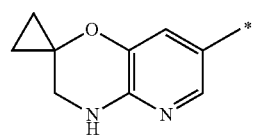

A.1e
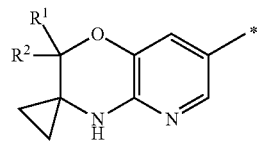

A.1f
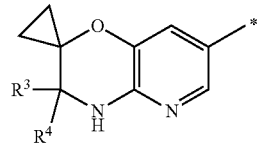

or a pharmaceutically acceptable salt thereof.

In another embodiment of the present invention A is formula A.1a.

In another embodiment of the present invention A is formula A.1b.

In another embodiment of the present invention A is formula A.1c.

In another embodiment of the present invention A is formula A.1d.

In another embodiment of the present invention A is formula A.1e.

In another embodiment of the present invention A is formula A.1f.

In another embodiment of the present invention A is selected from the group consisting of formulas A.1b or A.1c.

In another embodiment of the present invention A is selected from the group consisting of formulas A.1a or A1.d In another embodiment of the present invention A is selected from the group consisting of formulas A.1e or A.1f.

In another embodiment of the present invention A denotes a group of formula A.2

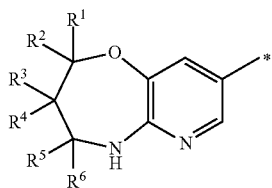
A.2

In another embodiment of the present invention

A is selected from the group consisting of formulas A.2a to A.2g

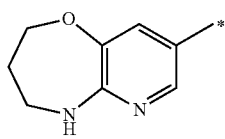
A.2a

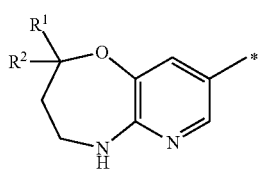
A.2b

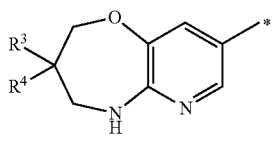
A.2c

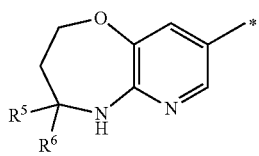
A.2d

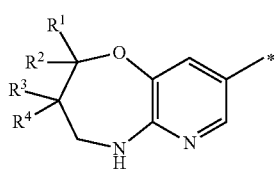
A.2e

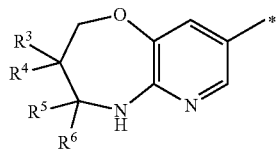
A.2f

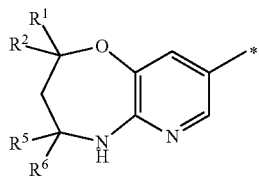
A.2g or a pharmaceutically acceptable salt thereof.

In another embodiment of the present invention A is formula A.2a.

In another embodiment of the present invention A is formula A.2b.

In another embodiment of the present invention A is formula A2c.

In another embodiment of the present invention A is formula A.2d.

In another embodiment of the present invention A is formula A.2e.

In another embodiment of the present invention A is formula A.2f.

In another embodiment of the present invention A is formula A.2g.

In another embodiment of the present invention A is selected from the group consisting of formulas A.2a and A.2b.

In another embodiment of the present invention A is selected from the group consisting of formulas A.2c and A.2d.

In another embodiment of the present invention A is selected from the group consisting of formulas A.2d and A.2e.

In another embodiment of the present invention A is selected from the group consisting of formulas A.2f and A.2g.

In another embodiment of the present invention

B denotes B.1 or B.2

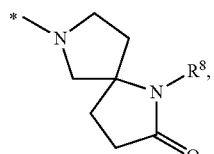
B.1

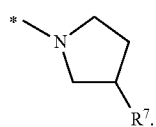
B.2

In another embodiment of the present invention
B denotes B.1

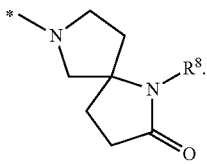
B.1

In another embodiment of the present invention
B denotes B.2

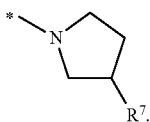
B.2

In another embodiment of the present invention
B denotes B.3

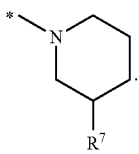
B.3

Another embodiment of the present invention are compounds of formula IA or the pharmaceutically acceptable salts thereof.

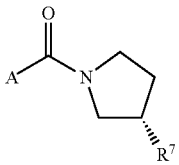
IA

Another embodiment of the present invention are compounds of formula IB or the pharmaceutically acceptable salts thereof.

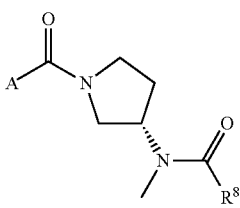
IB

Another embodiment of the present invention are compounds of formula IC or the pharmaceutically acceptable salts thereof

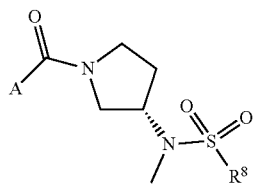
IC

Another embodiment of the present invention are compounds of formula ID or the pharmaceutically acceptable salts thereof

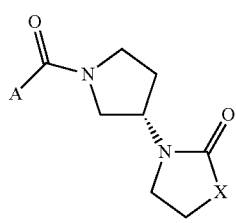
ID

In another embodiment of the present invention
each $R^1$ and $R^2$ is independently selected from the group consisting of
H, $CH_3$ and —$CH_2OH$;
In another embodiment of the present invention
$R^1$ is selected from the group $R^{1a}$ consisting of H, $CH_3$ and —$CH_2OH$.
In another embodiment of the present invention
$R^1$ is $R^{1.b}$ and $R^{1.b}$ denotes H.
In another embodiment of the present invention
$R^1$ is $R^{1c}$ and $R^{1c}$ denotes $CH_3$.
In another embodiment of the present invention
$R^1$ is $R^{1g}$ and $R^{1b}$ denotes —$CH_2OH$.
In another embodiment of the present invention
$R^2$ is selected from the group $R^{2a}$ consisting of H, $CH_3$ and —$CH_2OH$.
In another embodiment of the present invention
$R^2$ is $R^{2.b}$ and $R^{2.b}$ denotes H.
In another embodiment of the present invention
$R^2$ is $R^{2c}$ and $R^{2c}$ denotes $CH_3$.
In another embodiment of the present invention
$R^2$ is $R^{2d}$ and $R^{2d}$ denotes —$CH_2OH$.
In another embodiment of the present invention
$R^1$ or $R^2$ denotes H.
In another embodiment of the present invention
$R^1$ and $R^2$ together form a 3-4 membered carbocycle.
In another embodiment of the present invention
$R^1$ and $R^2$ together form cyclopropyl.
In another embodiment of the present invention
$R^1$ and $R^2$ together form cyclobutyl.
In another embodiment of the present invention
each $R^3$ and $R^4$ is independently selected from the group consisting of
H, $C_{1-3}$-alkyl and phenyl.
In another embodiment of the present invention
$R^3$ is $R^{3a}$ and $R^{3a}$ is selected from the group consisting of H, $C_{1-3}$-alkyl and phenyl.
In another embodiment of the present invention
$R^3$ is $R^{3b}$ and $R^{3b}$ denotes H.
In another embodiment of the present invention
$R^3$ is $R^{3c}$ and $R^{3c}$ is phenyl.

In another embodiment of the present invention
$R^3$ is $R^{3d}$ and $R^{3d}$ is selected from the group consisting of methyl, ethyl and propyl.

In another embodiment of the present invention
$R^4$ is $R^{4a}$ and $R^{4a}$ is selected from the group consisting of H, $C_{1-3}$-alkyl and phenyl.

In another embodiment of the present invention
$R^4$ is $R^{4b}$ and $R^{4b}$ denotes H In another embodiment of the present invention
$R^4$ is $R^{4c}$ and $R^{4c}$ is phenyl.

In another embodiment of the present invention
$R^4$ is $R^{4d}$ and $R^{4d}$ is selected from the group consisting of methyl, ethyl and propyl.

In another embodiment of the present invention
$R^3$ or $R^4$ denotes H.

In another embodiment of the present invention
$R^3$ and $R^4$ denotes H.

In another embodiment of the present invention
$R^3$ and $R^4$ together form a 3-4 membered carbocycle.

In another embodiment of the present invention
$R^3$ and $R^4$ together form cyclopropyl.

In another embodiment of the present invention
$R^3$ and $R^4$ together form cyclobutyl.

In another embodiment of the present invention
$R^5$ and $R^6$ denote H or
$R^5$ and $R^6$ together form a 3-4 membered carbocycle.

In another embodiment of the present invention
$R^5$ and $R^6$ denote H.

In another embodiment of the present invention
$R^5$ and $R^6$ together form a 3-4 membered carbocycle.

In another embodiment of the present invention
$R^5$ and $R^6$ together form cyclopropyl.

In another embodiment of the present invention
$R^5$ and $R^6$ together form cyclobutyl.

In another embodiment of the present invention
$R^7$ is 5-6 membered heteroaryl or
$R^7$ is selected from the group consisting of formulas $R^{7.a}$, $R^{7.b}$ and $R^{7.c}$;

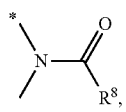

$R^{7.a}$

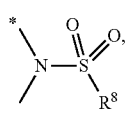

$R^{7.b}$

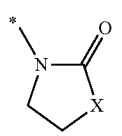

$R^{7.c}$

In another embodiment of the present invention
$R^7$ is $R^{7d}$ and $R^{7d}$ is selected from the group consisting of $C_{1-3}$-alkyl, halogen and $C_{1-3}$-alkoxy.

In another embodiment of the present invention
$R^7$ is $R^{7e}$ and $R^{7e}$ is selected from the group consisting of $R^{7a}$, $R^{7b}$ and $R^{7c}$.

In another embodiment of the present invention
$R^7$ is $R^{7f}$ and $R^{7f}$ denotes 6-membered heteroaryl.

In another embodiment of the present invention
$R^7$ is $R^{7g}$ and $R^{7g}$ denotes pyridinyl.

In another embodiment of the present invention
$R^7$ is $R^{7h}$ and $R^{7h}$ denotes 5-membered heteroaryl.

In another embodiment of the present invention
$R^8$ is selected from the group consisting of $C_{1-3}$-alkyl, $C_3$-$C_6$-cycloalkyl and 3-6 membered heterocyclyl;

In another embodiment of the present invention
$R^8$ is $R^{8a}$ and $R^{8a}$ is selected from the group consisting of methyl, cyclopropyl and oxetanyl.

In another embodiment of the present invention
$R^8$ is $R^{8b}$ and $R^{8b}$ is methyl.

In another embodiment of the present invention
$R^8$ is $R^{8c}$ and $R^{8c}$ is oxetanyl.

In another embodiment of the present invention
$R^8$ is $R^{8d}$ and $R^{8d}$ is cyclopropyl.

In another embodiment of the present invention
X is $CH_2$ or O.

In another embodiment of the present invention
X is $CH_2$.

In another embodiment of the present invention
X is O.

The following table represents further embodiments I.1 to I.9 of the compounds of formula I:

| I.1  | $R^{1b}$ | $R^{2a}$ |
| I.2  | $R^{1b}$ | $R^{2b}$ |
| I.3  | $R^{1b}$ | $R^{2c}$ |
| I.4  | $R^{1b}$ | $R^{2d}$ |
| I.5  | $R^{1a}$ | $R^{2b}$ |
| I.6  | $R^{1c}$ | $R^{2b}$ |
| I.7  | $R^{1d}$ | $R^{2b}$ |
| I.9  | $R^{3b}$ | $R^{4a}$ |
| I.10 | $R^{3b}$ | $R^{4b}$ |
| I.11 | $R^{3b}$ | $R^{4c}$ |
| I.12 | $R^{3b}$ | $R^{4d}$ |
| I.13 | $R^{4b}$ | $R^{3a}$ |
| I.14 | $R^{4b}$ | $R^{3c}$ |
| I.15 | $R^{3b}$ | $R^{3d}$ |

The following table represents further embodiments I.16 to I.21 of the compounds of formula I:

| I.16 | A.1 | B.1 |
| I.17 | A.1 | B.2 |
| I.18 | A.1 | B.3 |
| I.19 | A.2 | B.1 |
| I.20 | A.2 | B.2 |
| I.21 | A.2 | B.3 |

Any and each of the definitions of A, B, $R^1$, $R^2$, $R^3$, $R^4$, $R^5$, $R^6$, $R^7$, $R^8$ and X may be combined with each other.

A preferred embodiment of the current invention is a compound of the formula (I),

(I)

wherein
A is a group of formula A.1 or A.2:

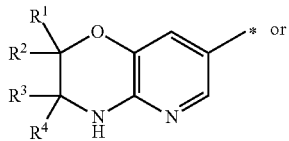
A.1

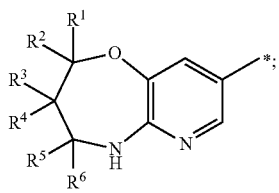
A.2

B is selected from the group consisting of formulas B.1, B.2 and B.3:

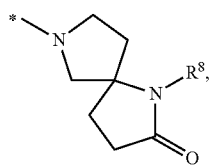
B.1

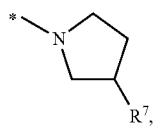
B.2

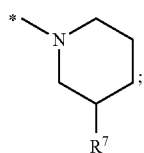
B.3 each $R^1$ and $R^2$ is independently selected from the group consisting of H, $CH_3$ and $-CH_2OH$;
each $R^3$ and $R^4$ is independently selected from the group consisting of H, $C_{1-3}$-alkyl and phenyl or
$R^3$ and $R^4$ together form cyclopropyl;
$R^5$ and $R^6$ denote H or
$R^5$ and $R^6$ together form cyclopropyl;
$R^7$ is 6-membered heteroaryl or
$R^7$ is selected from the group consisting of formulas $R^{7.a}$, $R^{7.b}$ and $R^{7.c}$;

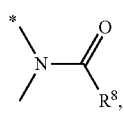
$R^{7.a}$

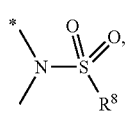
$R^{7.b}$

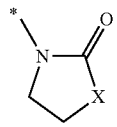
$R^{7.c}$ $R^8$ is selected from the group consisting of $C_{1-3}$-alkyl, $C_{3-6}$-cycloalkyl and 3-6 membered heterocyclyl;
X is $CH_2$ or O
or a pharmaceutically acceptable salt thereof.

A further preferred embodiment of the current invention is a compound of the formula (I),

(I)

wherein
A is a group of formula A.1 or A.2:

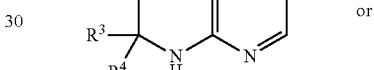
A.1 or

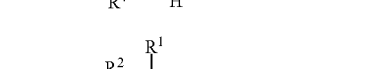
A.2

B is selected from the group consisting of formulas B.1, B.2 and B.3:

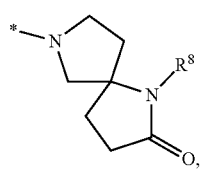
B.1

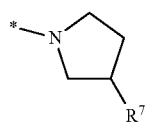
B.2

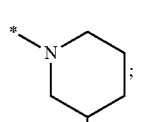
B.3 each $R^1$ and $R^2$ is independently selected from the group consisting of H, $CH_3$ and $-CH_2OH$;

each R³ and R⁴ is independently selected from the group consisting of H, $C_{1-3}$-alkyl and phenyl or R³ and R⁴ together form cyclopropyl;

R⁵ and R⁶ denote H or

R⁵ and R⁶ together form cyclopropyl.

R⁷ is pyridinyl or

R⁷ is selected from the group consisting of formulas $R^{7.a}$, $R^{7.b}$ and $R^{7.c}$;

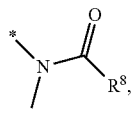

$R^{7.a}$

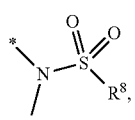

$R^{7.b}$

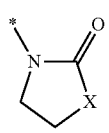

$R^{7.c}$

R⁸ is $R^{8a}$ and $R^{8a}$ is selected from the group consisting of methyl, cyclopropyl and oxetanyl.

X is $CH_2$ or O or a pharmaceutically acceptable salt thereof.

A further preferred embodiment of the current invention is a compound of the formula (I),
wherein
A is A.2,
B is B.2,
R¹ and R² denote hydrogen,
R³ and R⁴ denote hydrogen and
R⁵ and R⁶ together form cyclopropyl.
R⁷ is $R^{7.a}$ A further preferred embodiment of the current invention is a compound of the formula (I),
wherein
A is A.1,
B is B.2,
R¹ and R² denote hydrogen,
R³ and R⁴ together form cyclopropyl and
R⁷ is $R^{7.a}$ A further preferred embodiment of the current invention are the above compounds of formula I, selected from the group consisting of examples 14, 15, 16, 17, 21, 22, 25, 26, 37 and 42.

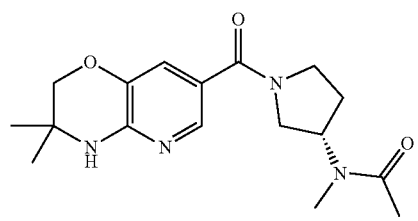

Ex. 14

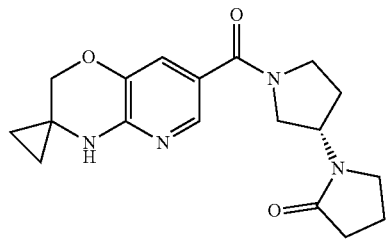

Ex.15

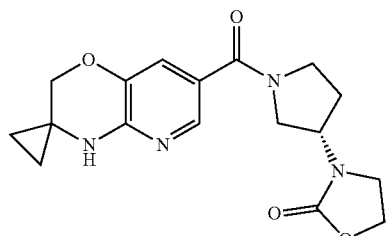

Ex. 16

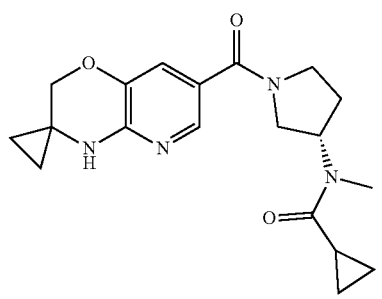

Ex.17

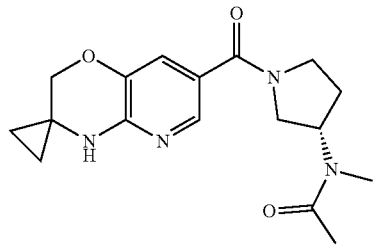

Ex.21

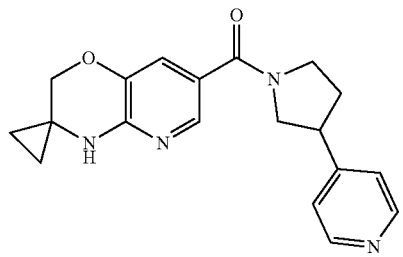

*Ex.22

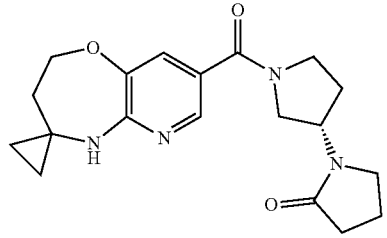

Ex.25

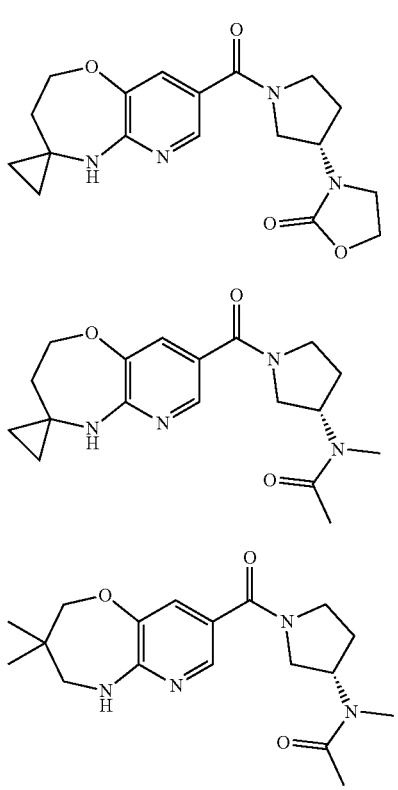

Ex.26

Ex.37

Ex.42 or a pharmaceutically acceptable salt thereof.

*The stereochemistry at the 3-position of the pyrrolidine-ring of the enantiomerically pure compound was not determined.

A further preferred embodiment of the current invention are the above compounds of formula I, selected from the group consisting of examples 14, 15, 16, 17, 21, 22, 25, 26, 37 and 42.

A further preferred embodiment of the current invention is the compound of example 14.

A further preferred embodiment of the current invention is the compound of example 15

A further preferred embodiment of the current invention is the compound of example 16.

A further preferred embodiment of the current invention is the compound of example 17.

A further preferred embodiment of the current invention is the compound of example 21.

A further preferred embodiment of the current invention is the compound of example 22.

A further preferred embodiment of the current invention is the compound of example 25.

A further preferred embodiment of the current invention is the compound of example 26.

A further preferred embodiment of the current invention is the compound of example 37.

A further preferred embodiment of the current invention is the compound of example 42.

A further preferred embodiment of the current invention are pharmaceutically acceptable salts of the above compounds of formula I, selected from the group consisting of examples 14, 15, 16, 17, 21, 22, 25, 26, 37 and 42.

A further preferred embodiment of the current invention are pharmaceutically acceptable salts of example 14.

A further preferred embodiment of the current invention are pharmaceutically acceptable salts of example 15.

A further preferred embodiment of the current invention are pharmaceutically acceptable salts of example 16.

A further preferred embodiment of the current invention are pharmaceutically acceptable salts of example 17.

A further preferred embodiment of the current invention are pharmaceutically acceptable salts of example 21.

A further preferred embodiment of the current invention are pharmaceutically acceptable salts of example 22.

A further preferred embodiment of the current invention are pharmaceutically acceptable salts of example 25.

A further preferred embodiment of the current invention are pharmaceutically acceptable salts of example 26.

A further preferred embodiment of the current invention are pharmaceutically acceptable salts of example 37.

A further preferred embodiment of the current invention are pharmaceutically acceptable salts of example 42.

A further embodiment of the current invention is a pharmaceutical composition comprising a therapeutically effective amount of at least one compound of formula I or a pharmaceutically acceptable salt thereof and one or more pharmaceutically acceptable excipients.

A further embodiment of the current invention is a compound of formula I or a pharmaceutically acceptable salt thereof for use as a medicament.

A further embodiment of the current invention is the use of a compound of formula I for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, colorectal cancer or pancreatic cancer related new onset diabetes.

A further embodiment of the current invention is the use of a compound of formula I for treating a patient suffering from Crohn's disease, ulcerative colitis, systemic sclerosis, Non-Alcoholic Steatohepathitis (NASH), chronic obstructive pulmonary disease or atopic dermatitis, preferably Crohn's disease, ulcerative colitis, systemic sclerosis, Non-Alcoholic Steatohepathitis (NASH) or atopic dermatitis, particularly preferred from Crohn's disease or ulcerative colitis.

A further embodiment of the current invention is the use of a compound of formula I for treating a patient suffering from moderate to severe Crohn's disease.

A further embodiment of the current invention is the use of a compound of formula I for treating a patient suffering from ulcerative colitis.

A further embodiment of the current invention is the use of a compound of formula I for treating a patient suffering from atopic dermatitis.

In a further embodiment, there is provided a method of treating a disease chosen from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, colorectal cancer and pancreatic cancer related new onset diabetes comprising administering to a patient a therapeutically effective amount of a compound according to the first embodiment or any of its related embodiments or a pharmaceutically acceptable salt thereof.

In a further embodiment, there is provided a process for preparation of a compound according to the first embodiment or any of its related embodiments by the methods shown herein below.

The actual pharmaceutically effective amount or therapeutic dosage will usually depend on factors known by those skilled in the art such as age and weight of the patient, route of administration and severity of disease. In any case the compounds will be administered at dosages and in a manner which allows a pharmaceutically effective amount to be delivered based upon patient's unique condition.

A further embodiment of the current invention is a pharmaceutical composition comprising additionally to a compound of formula I, a pharmaceutically active compound selected from the group consisting of an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists and methotrexate, but also combinations of two or three active substances.

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

An asterisk may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$-alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$) CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 2,2-dimethyl-1-propyl (neo-pentyl; —CH$_2$C (CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$), 2,3-dimethyl-1-butyl (—CH$_2$CH(CH$_3$)CH(CH$_3$) CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$ alkylamino or $C_{x-y}$ alkoxy.

Halogen relates to fluorine, chlorine, bromine and/or iodine atoms.

Cycloalkyl is made up of the subgroups monocyclic hydrocarbon rings, bicyclic hydrocarbon rings and spirohydrocarbon rings. The systems are saturated. In bicyclic hydrocarbon rings two rings are joined together so that they have at least two carbon atoms together.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl.

Corresponding groups are an example:

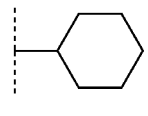

cyclohexyl

Spirocycle is a spiro-hydrocarbon ring one carbon atom (spiroatom) belongs to two rings together.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl and naphthyl.

The above definition of aryl also applies if aryl is part of another (combined) group as for example in arylamino, aryloxy or arylalkyl.

The term heterocycle or heterocyclyl denotes ring systems, which are derived from the previously defined cycloalkyl or spirocycle by replacing one or more of the groups —CH$_2$— independently of one another in the hydrocarbon rings by the groups —O—, —S— or —NH—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide).

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuranyl, tetrahydropyranyl, piperidinyl, piperazinyl, pyrrolidinyl, morpholinyl, or the following heterocyclic spirocycles

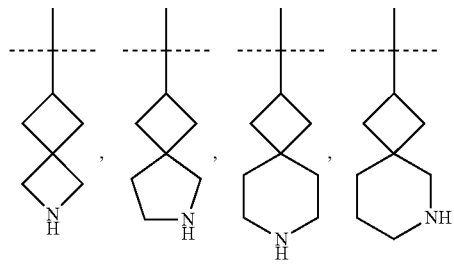

Heteroaryl denotes monocyclic heteroaromatic rings or polycyclic rings with at least one heteroaromatic ring, which compared with the corresponding aryl or cycloalkyl, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are pyridinyl, pyridazinyl, pyrimidinyl, pyrazinyl, benzoxazolyl, indolyl, isoindolyl, benzofuranyl, benzimidazolyl, benzothiazolyl, and the like.

Thus, the term "heteroaryl" includes the following exemplary structures which are not depicted as radicals as each form are optionally attached through a covalent bond to any atom so long as appropriate valences are maintained:

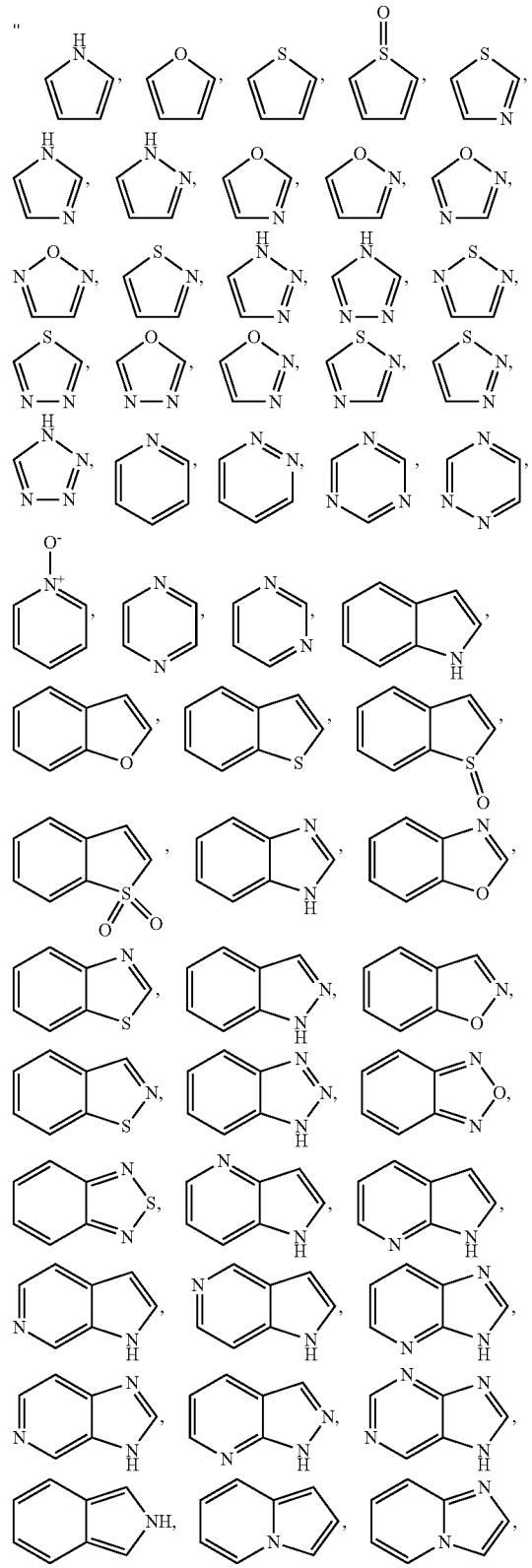

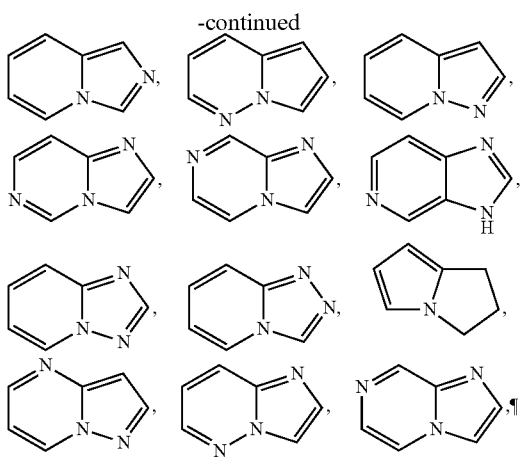

Heteroatoms may optionally be present in all the possible oxidation stages (sulphur→sulphoxide —SO—, sulphone —SO$_2$—; nitrogen→N-oxide).

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

All cyclic and acyclic systems defined in this section hereinabove shall be understood to be optionally partially or fully halogenated where possible and unless otherwise indicated.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts, preferably acid salts, thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

In a representation such as for example

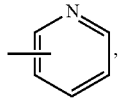

the solid line means that the ring system may be attached to the molecule via the carbon atom 1, 2 or 3, and is thus equivalent to the following representation

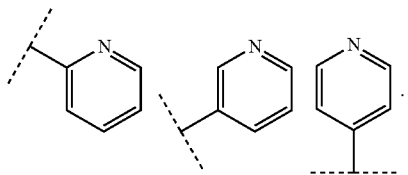

By a therapeutically effective amount for the purposes of this invention is meant a quantity of substance that is capable of obviating symptoms of illness or alleviating these symptoms, or which prolong the survival of a treated patient.

| List of abbreviations | |
|---|---|
| Ac | Acetyl |
| ACN | Acetonitrile |
| aq | Aqueous |
| Ar | Argon |
| ATP | adenosine triphosphate |
| Bn | Benzyl |
| Bu | Butyl |
| Boc | tert-butyloxycarbonyl |
| cat | Catalyst |
| CD | Crohn's disease |
| conc | concentrated |
| d | day(s) |
| DBU | 1,8-Diazabicyclo(5.4.0)undec-7-ene |
| DCM | Dichloromethane |
| DIEA | N,N-diisopropylethylamine |
| DMAP | 4-N,N-dimethylaminopyridine |
| DMA | Dimethylacetamide |
| DME | 1,2-dimethoxyethane |
| DMF | N,N-dimethylformamide |
| DMSO | Dimethylsulphoxide |
| dppf | 1,1'-bis(diphenylphosphino)ferrocene |
| EDC | 1-Ethyl-3-(3-dimethylaminopropyl)carbodiimide |
| ESI | electron spray ionization |
| Et | Ethyl |
| Et$_2$O | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| HWB assay | Human Whole Blood assay |
| i | Iso |
| IBD | Inflammatory Bowel Disease |
| IPAc | Isopropyl acetate |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf (R$_f$) | retention factor |
| RP | reversed phase |
| RT | Retention time (HPLC) |
| rt | ambient temperature |
| SFC | supercritical fluid chromatography |
| TBAF | tetrabutylammonium fluoride |
| TBDMS | tert-butyldimethylsilyl |
| TBDPS | tert-butyldiphenylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |

| List of abbreviations | |
|---|---|
| UC | Ulcerative colitis |
| UV | Ultraviolet |
| VNN-1 | Vanin-1 |
| VNN-2 | Vanin-2 |

Features and advantages of the present invention will become apparent from the following detailed examples which illustrate the fundamentals of the invention by way of example without restricting its scope:

Preparation of the Compounds According to the Invention

General Synthetic Methods

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid, 0.1% TFA, or 2.5 mM aqueous ammonium bicarbonate and used one of the following columns:

a) Waters Sunfire OBD C18 5 μm 30×150 mm column
b) Waters XBridge OBD C18 5 μm 30×150 mm column
c) Waters ODB C8 5 μm 19×150 mm column
d) Waters Atlantis ODB C18 5 μm 19×50 mm column
e) Waters Atlantis T3 OBD 5 μm 30×100 mm column
f) Phenomenex Gemini Axia C18 5 μm 30×100 mm column
g) Kinetex 1.7 um EVO C18, 50×2.1 mm HPLC Methods:

TABLE 1

Analytical HPLC Method A

| Method | Mobile Phase A | Mobile Phase B | Gradient Time (min) | % A | % B | Flow (mL/min.) | Column |
|---|---|---|---|---|---|---|---|
| A | 0.05% Formic Acid in 95% water/5% ACN | 0.05% Formic Acid in ACN | 0<br>1.19<br>1.70 | 90.0<br>0<br>0 | 10.0<br>100<br>100 | 0.8 | CSH C18 2.1 × 50 mm, 1.7 μm particle diameter |

TABLE 2

Analytical HPLC Method B

| Method | Mobile Phase A | Mobile Phase B | Gradient Time (min) | % A | % B | Flow (mL/min.) | Column |
|---|---|---|---|---|---|---|---|
| B | 0.05% Formic Acid in 95% water/5% ACN | 0.05% Formic Acid in ACN | 0<br>1.0<br>4.5<br>4.9 | 100<br>100<br>95.0<br>0 | 0<br>0<br>5.0<br>100 | 0.6 | HSS T3 2.1 × 100 mm, 1.8 um particle diameter |

TABLE 3

Analytical HPLC Method C

| Method | Mobile Phase A | Mobile Phase B | Gradient Time (min) | % A | % B | Flow (mL/min.) | Column |
|---|---|---|---|---|---|---|---|
| C | 2.5 mM ammonium bicarbonate in 95% water/5% ACN | ACN | 0<br>1.19<br>1.70 | 90.0<br>0<br>0 | 10.0<br>100<br>100 | 0.8 | (Ethylene Bridged Hybrid phase) BEH C18 2.1 × 50 mm, 1.7 um particle diameter |

TABLE 4

Analytical HPLC Method D

| Method | Mobile Phase A | Mobile Phase B | Gradient Time (min) | % A | % B | Flow (mL/min.) | Column |
|---|---|---|---|---|---|---|---|
| D | 2.5 mM ammonium bicarbonate in 95% water/5% ACN | ACN | 0<br>4.45<br>4.58 | 90.0<br>0<br>0 | 10.0<br>100<br>100 | 0.8 | (Ethylene Bridged Hybrid phase) BEH C18 2.1 × 50 mm, 1.7 um particle diameter |

TABLE 5

Analytical HPLC Method E (Z017_S04)
Method Name: E (Z017_S04)
Column: Stable Bond, 3 × 30 mm, 1.8 μm
Column Supplier: Agilent

| Gradient/Solvent Time [min] | % Sol [H2O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

TABLE 6

Analytical HPLC Method F (Z018_S04)
Method Name: F (Z018_S04)
Column: Sunfire, 3 × 30 mm, 2.5 μm
Column Supplier: Waters

| Gradient/Solvent Time [min] | % Sol [H2O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

TABLE 7

Analytical HPLC Method G (Z0111_S03)
Method Name: G (Z011_S03)
Column: XBridge C18, 3 × 30 mm, 2.5 μm
Column Supplier: Waters

| Gradient/Solvent Time [min] | % Sol [H2O, 0.1% NH3] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

TABLE 8

Analytical HPLC Method H

| Method | Mobile Phase A | Mobile Phase B | Gradient Time (min) | % A | % B | Flow (mL/min.) | Column |
|---|---|---|---|---|---|---|---|
| H | 0.05% Formic Acid in 95% water/5% ACN | 0.05% Formic Acid in ACN | 0 3.65 4.95 | 95 0 0 | 5 100 100 | 0.6 | HSS T3 2.1 × 100 mm, 1.8 um particle diameter |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme I below.

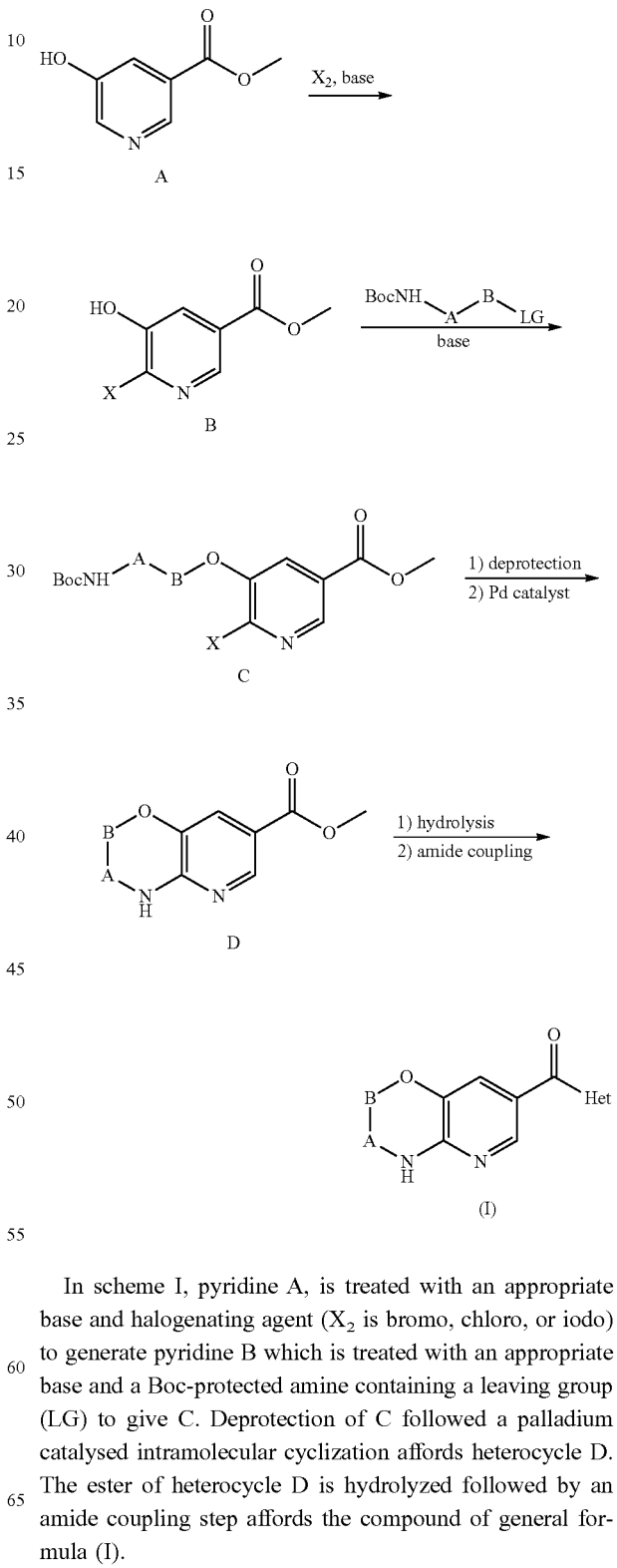

In scheme I, pyridine A, is treated with an appropriate base and halogenating agent ($X_2$ is bromo, chloro, or iodo) to generate pyridine B which is treated with an appropriate base and a Boc-protected amine containing a leaving group (LG) to give C. Deprotection of C followed a palladium catalysed intramolecular cyclization affords heterocycle D. The ester of heterocycle D is hydrolyzed followed by an amide coupling step affords the compound of general formula (I).

Synthetic Examples

Method A

Synthesis of Intermediate I-1

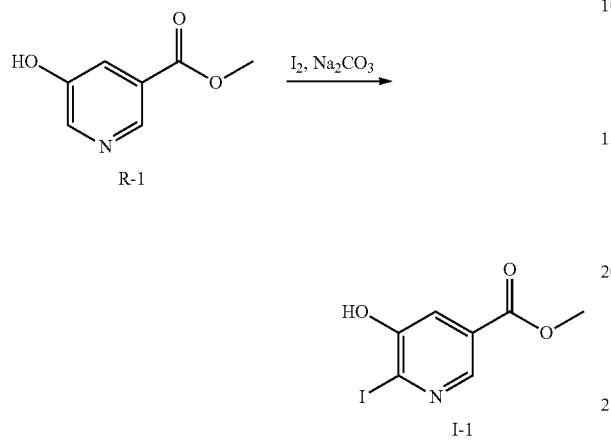

To a solution of R-1 (103 g, 671 mmol) in water (1.3 L) is added Na₂CO₃ (149 g, 1410 mmol) followed by iodine (170 g, 671 mmol). The reaction is stirred overnight at ambient temperature then neutralized with concentrated HCl. The solid is filtered, collected, and dried to afford I-1 (161 g, 86%) m/z=280.7 [M+H], $R_f$=0.4 (SiO2, EtOAc/petrol ether 3/7)

Method B

Synthesis of Intermediate I-2

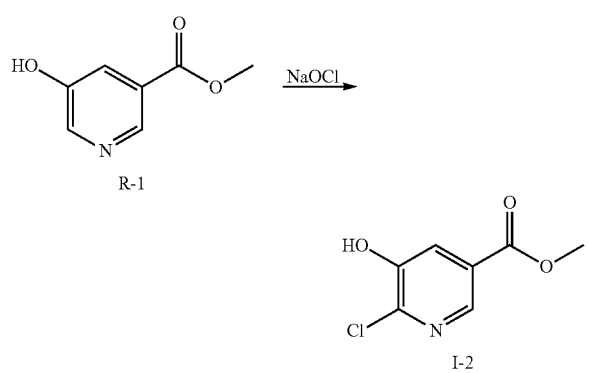

To a cold (0° C.) vessel containing R-1 (5.00 g, 33 mmol) is added an aqueous (6% by wt) solution of sodium hypochlorite (30 mL). The mixture is stirred for 30 min then treated with 1M aqueous HCl (50 mL) and stirred overnight. Additional aqueous sodium hypochlorite is added followed by stirring for 8 h then solid is filtered, collected, and dried to afford I-2 (1.8 g, 27%), m/z=188.0 [M+H], $R_f$=0.6 (SiO2, EtOAc/petrol ether 1/1)

Method C-1

Synthesis of Intermediate I-5

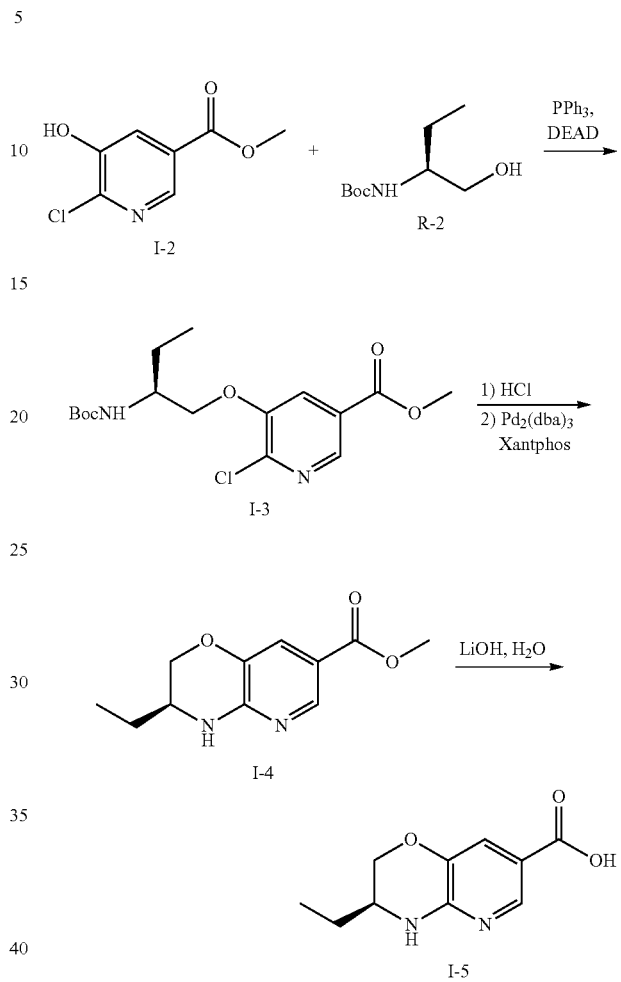

A mixture of I-2 (100 mg, 0.53 mmol), R-2 (111 mg, 0.59 mmol), and triphenylphosphine (210 mg, 0.80 mmol) is treated with DEAD (0.13 mL, 0.80 mmol) and stirred at ambient temperature for 2 h. The mixture is concentrated the purified by flash chromatography (SiO₂, 0-20% EtOAc in Hep) to afford I-3 (181 mg, 95%). A solution of I-3 (181 mg, 0.5 mmol) in dioxane (4 mL) is treated with a 4.0M HCl solution in dioxane (1.0 mL). The mixture is concentrated in vacuo to afford the free amine (114 mg, 0.44 mmol) which is dissolved in dioxane (10 mL) then treated with Pd₂(dba)₃ (40 mg, 0.044 mmol), 9,9-dimethyl-4,5-bis(diphenylphosphino)xanthene (51 mg, 0.088 mmol) and Cs₂CO₃ (431 mg, 1.3 mmol). The mixture is heated at 80° C. overnight then cooled and poured into water, extracted with EtOAc, and concentrated in vacuo to afford a mixture of I-4 and I-5. The mixture is treated with MeOH (1 mL), water (0.25 mL) and LiOH—H₂O (10 mg) and heated at 60° C. for 4 h. Mixture is cooled to ambient temperature then poured into water, acidified with 1 M aqueous HCl and extracted with EtOAc to give after concentration in vacuo I-5 (105 mg, 84%), m/z=209.02 [M+H], RT=0.41 min (HPLC-Method A)

The following intermediates are prepared in similar fashion from the appropriate Boc-protected amino alcohols:

| Structure | Intermediate | m/z | RT |
|---|---|---|---|
| (3-isopropyl-3,4-dihydro-2H-pyrido[3,2-b][1,4]oxazine-7-carboxylic acid, one enantiomer) | I-6 | 222.6 [M + H]20 | 0.43 (HPLC-Method A) |
| (3-isopropyl-3,4-dihydro-2H-pyrido[3,2-b][1,4]oxazine-7-carboxylic acid, other enantiomer) | I-7 | 222.7 [M + H] | 0.44 (HPLC-Method A) |
| (3-ethyl-3,4-dihydro-2H-pyrido[3,2-b][1,4]oxazine-7-carboxylic acid) | I-8 | 208.7 [M + H] | 0.33 (HPLC-Method A) |
| (3-methyl-3,4-dihydro-2H-pyrido[3,2-b][1,4]oxazine-7-carboxylic acid, one enantiomer) | I-9 | 195.0 [M + H] | 0.27 (HPLC-Method A) |
| (3-methyl-3,4-dihydro-2H-pyrido[3,2-b][1,4]oxazine-7-carboxylic acid, other enantiomer) | I-10 | 195.7 [M + H] | 1.61 (HPLC-Method B) |
| (2-methyl-3,4-dihydro-2H-pyrido[3,2-b][1,4]oxazine-7-carboxylic acid, one enantiomer) | I-11 | 195.0 [M + H] | 1.46 (HPLC-Method A) |
| (2-methyl-3,4-dihydro-2H-pyrido[3,2-b][1,4]oxazine-7-carboxylic acid, other enantiomer) | I-12 | 195.2 [M + H] | 0.29 (HPLC-Method A) |
| (3-phenyl-3,4-dihydro-2H-pyrido[3,2-b][1,4]oxazine-7-carboxylic acid) | I-13 | 257.0 [M + H] | 0.59 (HPLC-Method A) |

| Structure | Intermediate | m/z | RT |
|---|---|---|---|
| 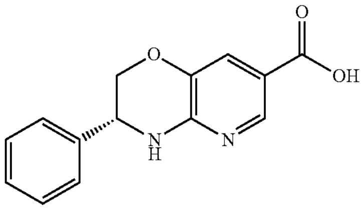 [SMILES: O=C(O)c1cnc2c(c1)OC[C@@H](c1ccccc1)N2] | I-14 | 256.7 [M + H] | 0.62 (HPLC-Method A) |
| 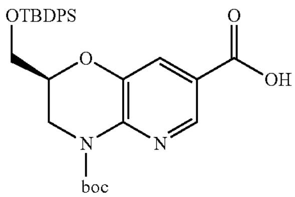 | I-15 | 549.3 [M + H] | 0.94 (HPLC-Method C) |

Method C-2

Synthesis of Intermediate I-16

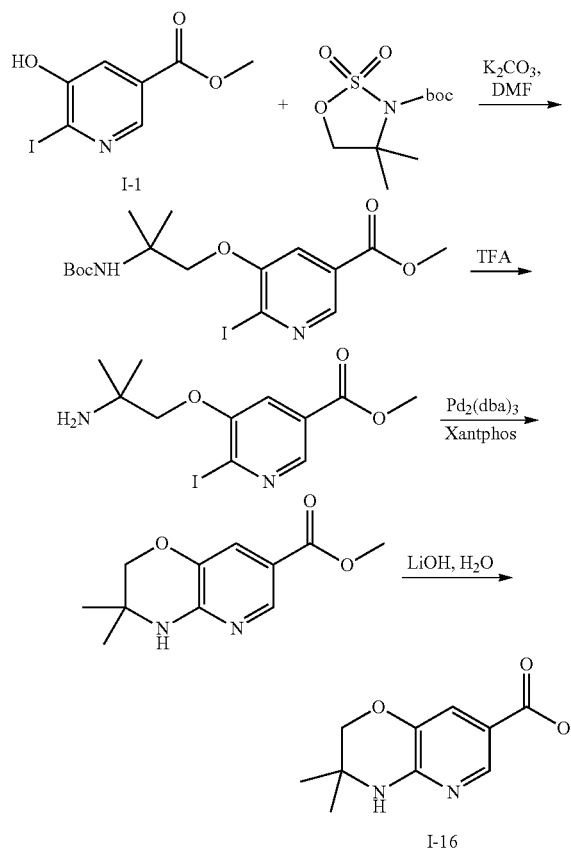

To a mixture of methyl 5-hydroxy-6-iodopyridine-3-carboxylate (6.66 g; 23.9 mmol) and DMF (45 ml) at rt is added K₂CO₃ (3.63 g; 26.3 mmol) and the mixture is stirred for 5 min at rt before tert-butyl 4,4-dimethyl-2,2-dioxo-oxathiazolidine-3-carboxylate (4.50 g; 17.9 mmol) is added and the reaction heated to 70° C. After stirring for 1.5 h the mixture is cooled to rt and another 4.50 g (17.9 mmol) tert-butyl 4,4-dimethyl-2,2-dioxo-oxathiazolidine-3-carboxylate are added. The reaction temperature is raised again to 70° C. and stirring is continued overnight. The reaction mixture is cooled to rt and poured onto 600 mL of water. The aqueous layer is extracted twice with EtOAc. The organics layers are combined, washed with aq. K₂CO₃ solution (15%), filtered over activated charcoal and the solvent is removed in vacuo. The remaining crude product is used without further purification.

The above mentioned crude product is added to 140 mL DCM and stirred at rt before 28 mL TFA is added. Stirring is continued for 2 h at rt. Then the solvent is removed in vacuo and to the residue are added 50 mL of saturated aq. NaHCO₃-solution. Further solid NaHCO₃ (5 g) is added And the aq. mixture is extracted twice with 150 mL EtOAc. The organic layers are combined and the solvent is removed in vacuo. The remaining crude product is triturated with diisopropylether.

m/z=351 [M+H], RT=0.73 min (HPLC-Method E)

The above mentioned product is added to dioxane (112 mL) and charged with 20.4 g (62.5 mmol) cesium carbonate. After degassing 1.94 g Pd2(dba)3 (2.09 mml) and 1.21 g (2.09) Xantphos are added and the mixture is stirred at 70° C. for 3 h. After that the reaction mixture is poured onto 500 mL water and extracted twice with EtOAc. The organic layers are combined, filtered over activated charcoal and the solvent is removed in vacuo. The remaining crude product is purified by column chromatography (SiO2, petrol ether/EtOAc 70/30→50/50).

m/z=223 [M+H], RT=0.68 min (HPLC-Method E)

The above mentioned product (1.90 g, 8.55 mmol) are added to a solution of 307.8 mg LiOH (12.8 mmol) in 25 mL of water. Then 30 mL methanol are added. The mixture is stirred at 50° C. for 3 h. Methanol is removed in vacuo and the mixture is further diluted with 50 mL of water. After that 12.8 mL of an aq. HCl-solution (conc.=1 mol/L) are added and the mixture is cooled down by using an ice bath and stirred for 30 min. After that, the precipitate is filtered, washed with cold water and dried in vacuo over 48 h at 40° C. to yield I-16 (1.90 g, 7.73 mmol).

m/z=209 [M+H], RT=0.58 min (HPLC-Method E)

Method D

Synthesis of Intermediate I-20

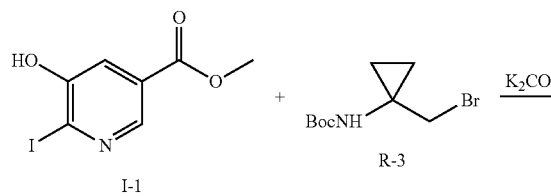

I-1    R-3

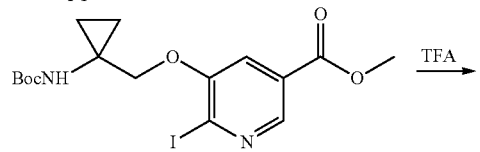

I-17

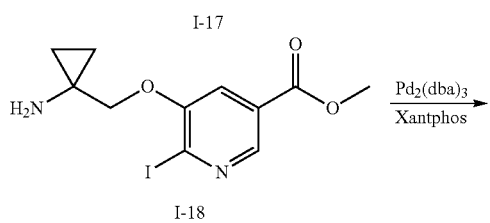

I-18

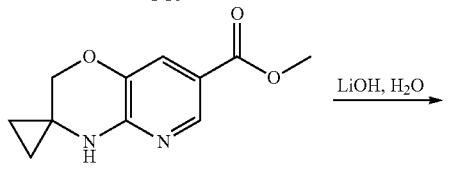

I-19

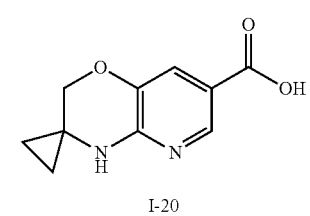

I-20

To a solution of I-1 (40 g, 143 mmol) in acetone (1 L) and DMF (60 mL) is added K₂CO₃ (59 g, 430 mmol) and R-3 (52 g, 208 mmol). The mixture is heated at 70° C. overnight then cooled to ambient temperature and slowly added to water (2.5 L). The resulting solids are filtered, collected and dried to afford I-17 (53 g, 83%). To a solution of I-17 (53 g, 119 mmol) in CH₂Cl₂ (500 mL) is added TFA (104 g, 913 mmol). The mixture is stirred at ambient temperature overnight then concentrated in vacuo to afford the free amine I-18 (33.6 g, 81%). m/z=349 [M+H], RT=0.70 min (HPLC-Method E).

Amine I-18 (66 g, 190 mmol) is dissolved in dioxane (300 mL) then treated with Pd₂(dba)₃ (8.7 g, 9.5 mmol), 9,9-dimethyl-4,5-bis(diphenylphosphino)xanthene (11 g, 19 mmol) and Cs₂CO₃ (185 g, 569 mmol) and heated at 100° C. for 1 h. The mixture is cooled to ambient temperature then diluted with EtOAc (500 mL), filtered through Celite and concentrated in vacuo. The residue is dissolved in 10% MeOH in CH₂Cl₂ (100 mL) and filtered through a pad of silica gel eluting with 2 L of 10% MeOH in CH₂Cl₂ then concentrated in vacuo. The residue is dissolved in CH₂Cl₂ (150 mL) and slowly poured into 1.5 L of heptane. The resulting solid is filtered, collected and dried to give I-19 (27.3 g, 65%). Ester I-19 (27.3 g, 124 mmol) is dissolved in THF (200 mL) and water (100 mL) and treated with LiOH (5.9 g, 248 mmol). The mixture is stirred at ambient temperature overnight then THF is removed in vacuo and solid is filtered. The aqueous filtrate is acidified with 4M aqueous HCl until neutral and solid is filtered. All solids are collected and dried to afford I-20 (21.4 g, 84%), m/z=207.9 [M+H], RT=0.59 min (HPLC-Method E)

The following intermediates are prepared in similar fashion from the appropriate Boc-protected amino alcohols:

| Structure | Intermediate | m/z | RT |
|---|---|---|---|
| 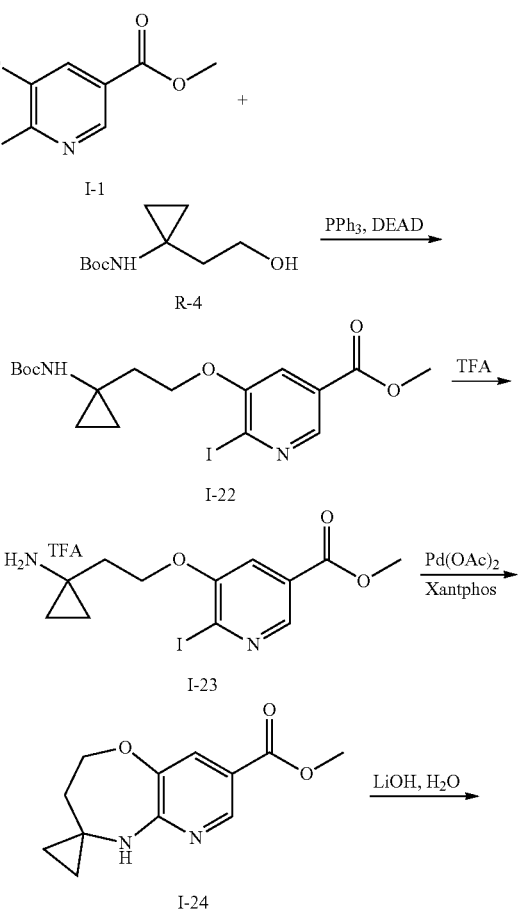 | I-21 | 195.0 [M + H] | 0.80 min (HPLC-method H) |

Method E

Synthesis of Intermediate I-25

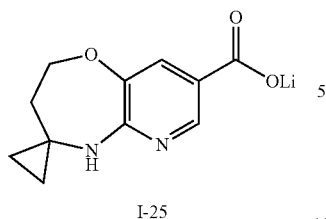

I-25

To a solution of I-1 (80 g, 287 mmol) and R-4 (63.5 g, 315 mmol) in THF (900 mL) is added a solution of triphenylphosphine (113 g, 430 mmol) and DEAD (196 mL, 430 mmol) in THF (300 mL). The mixture is stirred at ambient temperature for 1 h then concentrated in vacuo. The residue is triturated with $Et_2O$ (600 mL) and filtered through a pad of silica gel. The filtrate is concentrated then triturated with EtOAc (200 mL). The solid is filtered, collected and dried to give I-22 (102 g, 77%). To a solution of I-22 (102 g, 221 mmol) in MeOH (200 mL) is added TFA (1 L). The mixture is heated at 60° C. for 4 h then concentrated in vacuo to afford a residue that is triturated with $Et_2O$. The resulting solid is filtered, collected and dried to give TFA salt I-23 (101 g, 96%). m/z=363.2 [M+H], RT=0.38 min (HPLC-Method A)

To a solution of I-23 (50 g, 106 mmol) in DMA (500 mL) is added $Cs_2CO_3$ (93 g, 285 mmol) followed by $Pd(OAc)_2$ (1.9 g, 8.5 mmol) and 9,9-dimethyl-4,5-bis(diphenylphosphino)xanthene (4.9 g, 8.5 mmol). The mixture is heated at 90° C. for 2 h then cooled and filtered through Celite. The filtrate is concentrated in vacuo then filtered through a pad of silica gel with 25% EtOAc in Hep. The filtrate is concentrated in vacuo then triturated with $Et_2O$/Hep. The solid is filtered, collected and dried to give I-24 (17 g, 69%). A solution of I-24 (45 g, 192 mmol) in EtOH (600 mL) is treated with LiOH (6 g, 251 mmol) and mixture is heated at 80° C. for 1 h then cooled and filtered to remove insoluble. The filtrate is concentrated and resulting solid is triturated with EtOAc then solid is filtered, collected and dried to give I-25 (43 g, 99%) m/z=221.1 [M+H], RT=0.62 min (HPLC-Method F).

The following intermediate is prepared in similar fashion from the appropriate Boc-protected amino alcohols:

| Structure | Intermediate | m/z | RT |
|---|---|---|---|
| (structure shown) | I-26 | 223.0 [M + H] | 0.54 (HPLC-Method A) |

Method F

Synthesis of Intermediate I-28

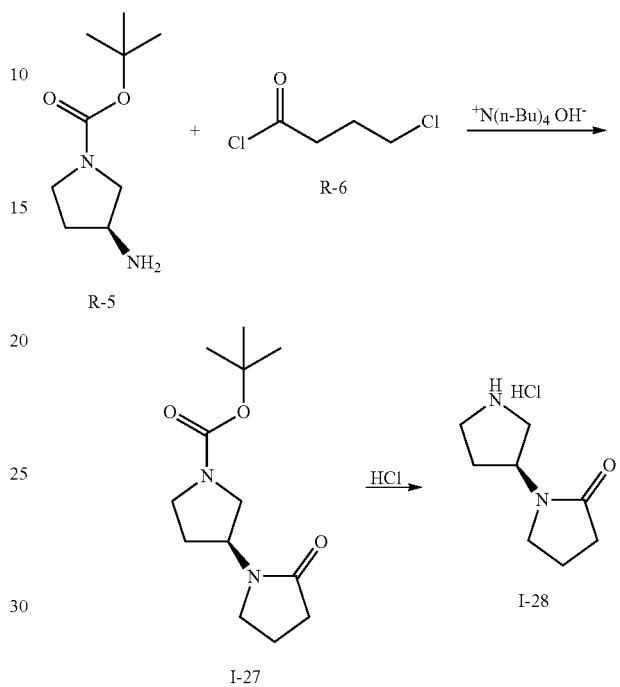

To a solution of R-5 (10.0 g, 54 mmol) in $CH_2Cl_2$ (80 mL) and 50% aqueous NaOH (21 mL) is added R-6 (6.8 g, 48 mmol). The mixture is stirred for 3 h then treated with a 1.5M aqueous solution of tetrabutylammonium hydroxide (36 mL) and stirred an additional 15 h. The mixture is then diluted with water, extracted with $CH_2Cl_2$, dried over $Na_2SO_4$, filtered, and concentrated to afford a residue that is purified by flash chromatography ($SiO_2$, 1.5% MeOH in $CH_2Cl_2$) to give I-27 (10 g, 73%), m/z=255.0 [M+H], RT=0.83 min (HPLC-Method G).

The Boc-amine I-27 (82 g, 322 mmol) is dissolved in dioaxane (150 mL) and treated with a 4.0M HCl solution in dioxane (240 mL). The mixture is stirred for 4 h then volatiles are removed in vacuo to give I-28 (58.4 g, 95%) m/z=155.0 [M+H], RT=0.27 min (HPLC-Method G)

The following intermediate is prepared in similar fashion from 2-chloroethyl chloroformate:

| Structure | Intermediate | m/z | RT |
|---|---|---|---|
| (structure shown) | I-29 | 157.8 [M + H] | 0.21 min (HPLC-Method G) |

Method G

Synthesis of Example 21

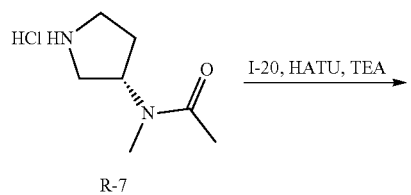

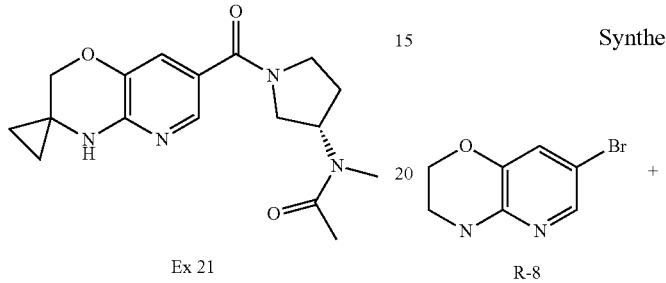

To a solution of I-20 (50.0 g, 242 mmol) in DMF (500 mL) is added R-7 (47.7 g, 267 mmol), TEA (73.6 g, 727 mmol), and HATU (101 g, 267 mmol). The mixture is stirred overnight then filtered through Celite and concentrated in vacuo. The residue is purified through a pad of silica gel eluting with EtOAc then 15% MeOH in EtOAc to afford a residue that is passed through a pad of KP—NH silica gel eluting with 10% MeOH in EtOAc. Purification by SFC (Luna HILIC column, 20% IPA in $CO_2$ at 40° C. and 140 bar) provides Ex 21 (21.6 g, 28%).

The following examples are made in similar fashion from the appropriate acid intermediates in Method C-E: Ex 1, 2, 4, 9, 13, 14, 29, 30, 31, 32, 35, 41.

Method H

Synthesis of Example 37

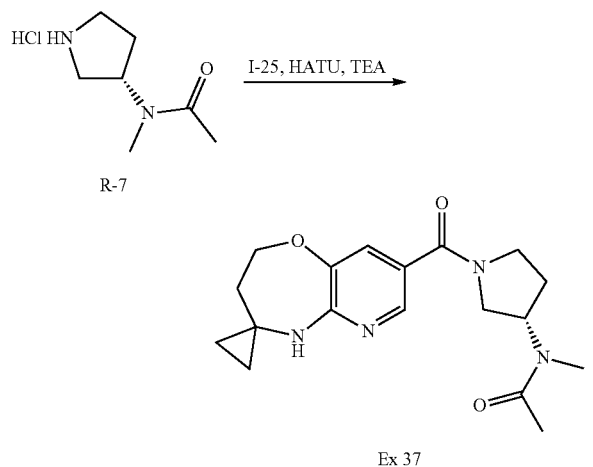

To a solution of I-25 (79 g, 359 mmol), HATU (150 g, 395 mmol) and R-7 (83 g, 466 mmol) in DMA (400 mL) is added TEA (99 mL, 717 mmol). The mixture is stirred for 30 min then concentrated in vacuo to afford a residue that is passed through a pad of silica gel eluting with EtOAc. The resulting residue after removal of the volatiles is passed through a pad of KP—NH silica gel eluting with 10% MeOH in EtOAc. The resulting residue after removal of the volatiles is triturated with acetone then solid is filtered, collected and dried to give Ex 37 (40 g, 32%).

The following example is made in similar fashion from the appropriate acid intermediates in Method C-E: Ex 42.

Method I

Synthesis of Example 3

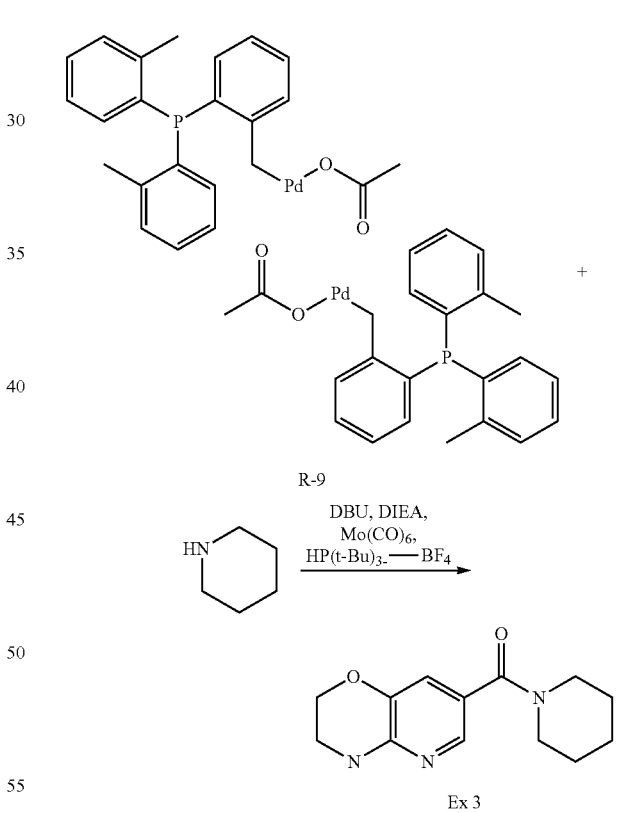

To a microwave vial is added R-8 (100 mg, 0.47 mmol), R-9 (44 mg, 0.047 mmol), HP(t-Bu)$_3$-BF$_4$ (27 mg, 0.093 mmol), Mo(CO)$_6$ (123 mg, 0.47 mmol) and piperidine (0.14 mL, 1.4 mmol). Contents are dissolved in dioxane (3 mL) then treated with DBU (0.14 mL, 0.93 mmol) and DIEA (0.33 mL, 1.86 mmol) and heated at 150° C. in the microwave for 30 min. The mixture is cooled to ambient temperature then filtered through a pad of Celite, concentrated and purified by RHPLC to give Ex 3 (35 mg, 30%).

Method J

Synthesis of Example 22

The racemic compound R-11 can be separated into the enatiomerically pure R-10 and R-12 by preparative SFC using the following conditions:

Preparative SFC Method:
Column: 2.0×25.0 cm ChromegaChiral CCS from ES Industries (West Berlin, N.J.)
$CO_2$ Co-solvent: Isopropanol with 0.25% isopropylamine
Isocratic method: 25% Co-solvent at 80 g/min.
System pressure: 115 bar
Column temp.: 25° C.
Sample dilutent: isopropanol.
Analytical SFC method
Column: 4.6×100 mm ChromegaChiral CCS from ES Industries (West Berlin, N.J.)
$CO_2$ Co-solvent: Isopropanol with 0.1% isopropylamine
Isocratic method: 15% Co-solvent at 4 mL/min.
System pressure: 180 bar
Column temp.: 25° C.
Sample dilutent: isopropanol.
R-10:
RT=3.2 min (analytical SFC method)
R-12:
RT=4.6 min (analytical SFC method)
*The absolute configuration of the enantiomerically pure R-10 and R-12 was not determined.

To a solution of I-20 (30 mg, 0.15 mmol), HATU (61 mg, 0.16 mmol) and R-10 (24 mg, 0.16 mmol) in DMA (2 mL) is added DIEA (0.1 mL, 0.6 mmol). The mixture is stirred for 1 h then purified by RHPLC to give *Ex 22 (12 mg, 24%).

The following examples are prepared in similar fashion from the appropriate acids and amines:

| Example | Acid | Amine |
|---|---|---|
| 5 | I-5 | R-11 |
| 6 | I-8 | R-11 |
| 7 | I-14 | R-11 |
| 8 | I-7 | R-11 |
| 10 | I-6 | R-11 |
| *11 | I-13 | R-12 |
| *12 | I-13 | R-10 |
| *20 | I-20 | R-12 |
| 28 | I-10 | R-13 |
| 33 | I-11 | R-11 |
| 34 | I-12 | R-11 |
| 40 | I-9 | R-11 |

*The stereochemistry at the 3-position of the pyrrolidine-ring of the enantiomerically pure compound was not determined.

Method K

Synthesis of Example 15

To a solution of I-20 (100 mg, 0.47 mmol), HATU (197 mg, 0.52 mmol) and I-28 (180 mg, 0.94 mmol) in DMF (1 mL) is added DIEA (0.4 mL). The mixture is stirred for 1 h then concentrated and passed through a pad of KP—NH silica gel eluting with EtOAc up to 10% (28% aqueous ammonium hydroxide) MeOH in EtOAc to give the title Ex 15 (84 mg, 52%).

The following examples are prepared in similar fashion from the appropriate acids and amines:

| Example | Acid | Amine |
|---------|------|-------|
| 16 | I-20 | I-29 |
| 25 | I-25 | I-28 |
| 26 | I-25 | I-29 |

Method L

Synthesis of Example 17

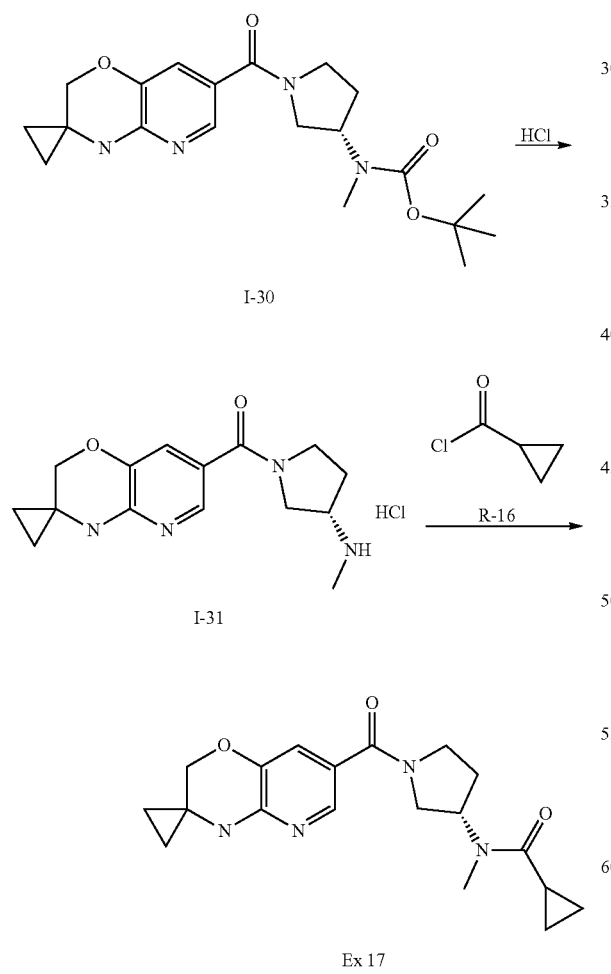

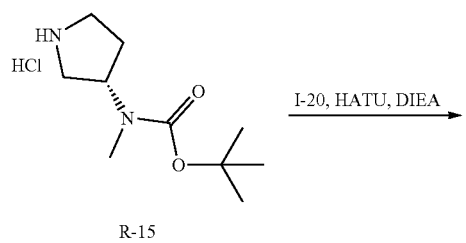

To a solution of I-20 (100 mg, 0.47 mmol) in DMF (1 mL) and DIEA (0.3 mL) is added R-15 (223 mg, 0.94 mmol) followed by HATU (197 mg, 0.52 mmol). The mixture is stirred for 1 h then concentrated and passed through a pad of KP—NH silica gel eluting with EtOAc up to 5% (28% aqueous ammonium hydroxide) MeOH in EtOAc to give I-30 which is dissolved in CH$_2$Cl$_2$ (5 mL) and treated with a 4.0 M HCl solution in dioxane (3 mL). The mixture is stirred overnight then concentrated in vacuo to give I-31 (153 mg, 0.47 mmol) that is dissolved in CH$_2$Cl$_2$ (10 mL) and TEA (2 mL). This mixture is treated with R-16 (49 mg, 0.47 mmol), stirred overnight then concentrated in vacuo and passed through a pad of KP—NH silica gel eluting with EtOAc up to 5% (28% aqueous ammonium hydroxide) MeOH in EtOAc to give Ex 17 (67 mg, 40%).

The following examples are prepared in similar fashion from I-31 and the appropriate acylating agent:

| Example | Acid Chloride |
|---------|---------------|
| 19 | R-17 |

Method M

Synthesis of Example 18

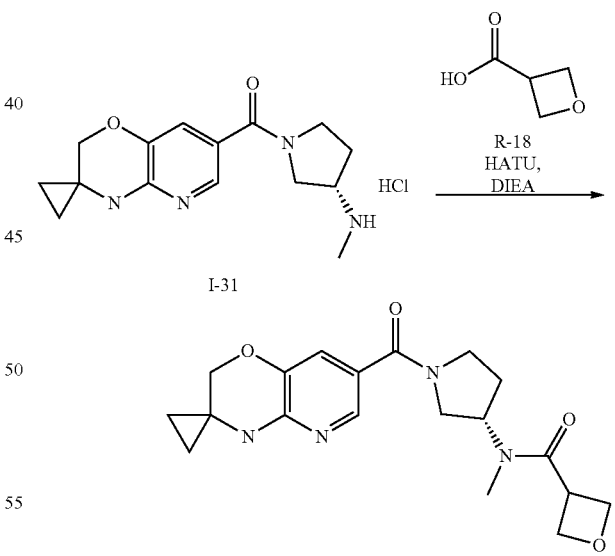

To a solution of I-31 (130 mg, 0.4 mmol) and R-18 (53 mg, 0.52 mmol) in DMF (3 mL) and DIEA (129 mg, 1 mmol) is added HATU (183 mg, 0.48 mmol). The mixture is stirred overnight then concentrated and passed through a pad of KP—NH silica gel eluting with EtOAc up to 10% (28% aqueous ammonium hydroxide) MeOH in EtOAc to give Ex 18 (45 mg, 30%).

Method N

Synthesis of Examples 23 and 24

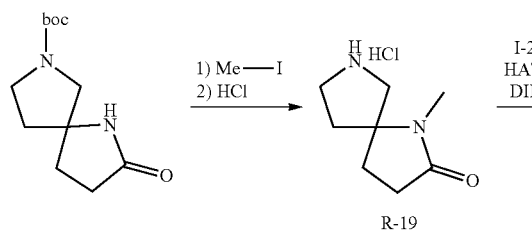

R-19

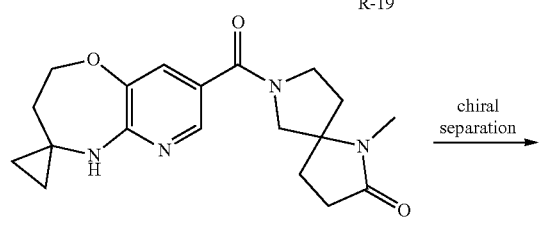

Ex 27

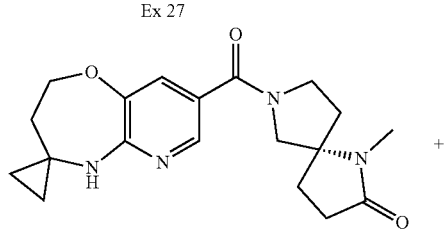

Ex 23

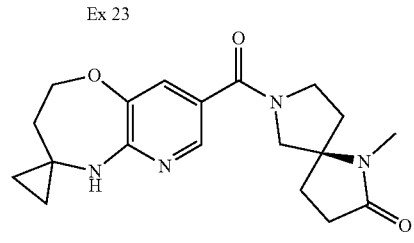

Ex 24

To a stirred solution of tert-butyl 2-oxo-1,7-diazaspiro[4,4]nonane-7-carboxylate (500 mg, 2.1 mmol) in 2 mL DMF was added 91.5 mg (24.0 mmol) NaH at 0° C. After 15 min 383.9 mg (2.7 mmol) iodomethane was added and the reaction was stirred overnight. The solvent was removed in vacuo and the residue was taken up in EtOAc and washed with water. The solvent was removed in vacuo and the crude product was used without further purification.

The above mentioned product is charged with 2.5 mL of a 4 M HCl-solution in dioxane and stirred at rt overnight. The solvent is removed in vacuo and the residue is triturated with DCM to yield R-19 (402 mg, 2.1 mmol), m/z=155.0 [M+H], RT=0.29 min (HPLC-Method G).

To a solution of I-25 (180 mg, 0.82 mmol) in DMA (5 mL) is added HATU (342 mg, 0.90 mmol) and the mixture is stirred for 30 min. This solution is then added to a solution of DIEA (317 mg, 2.5 mmol) and R-19 (203 mg, 1.1 mmol) in DMA (5 mL). The mixture is stirred for 15 min then concentrated in vacuo and purified by RHPLC to give Ex 27 (206 mg, 71%).

Ex 23 and Ex 24 are obtained by chiral SFC separation of Ex 27 using a 2.0×25.0 cm Chromegachiral CCS column from ES Industries and $CO_2$ with 45% MeOH containing 0.25% isopropyl amine at 80 g/min and a pressure and temperature of 120 bar and 25° C. respectively.

Method O

Synthesis of Example 39

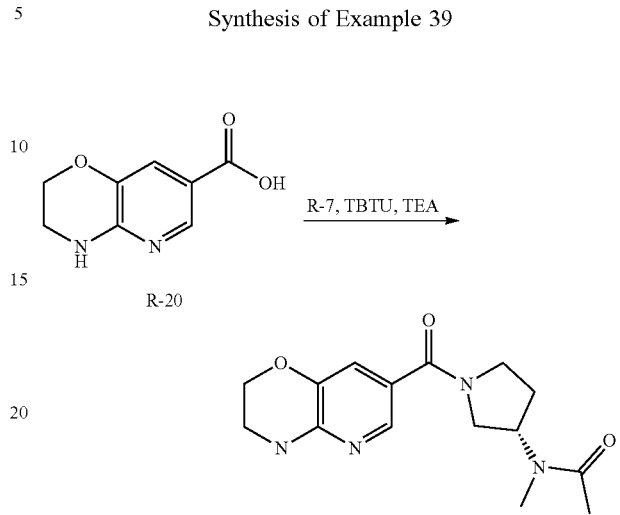

R-20

Ex 39

To a solution of R-20 (44 mg, 0.24 mmol), R-7 (48 mg, 0.27 mmol) and TBTU (94 mg, 0.29 mmol) in $CH_3CN$ (2 mL) is added TEA (0.12 mL). The mixture is stirred overnight then concentrated in vacuo and purified by RHPLC to give Ex 39 (49 mg, 66%).

The following example is prepared in similar fashion from the appropriate amine:

| Example | Acid | Amine |
|---------|------|-------|
| *38     | R-20 | R-10  |

*The stereochemistry of the enantiomerically pure compound was not determined.

Method P

Synthesis of Example 43

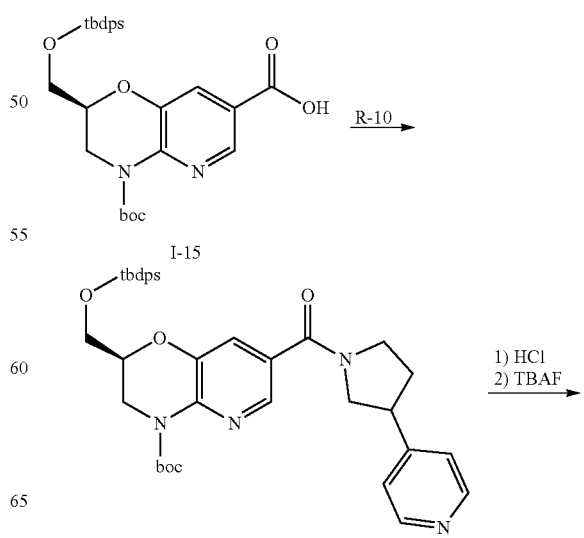

R-10

I-15

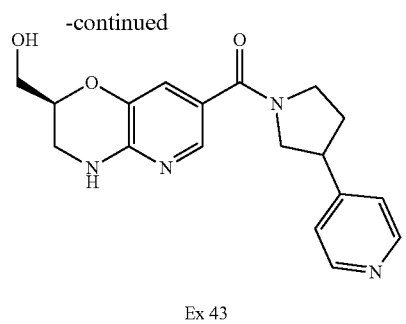

Ex 43

A mixture of acid I-15 (132 mg, 0.24 mmol), amine R-10 (39 mg, 0.26 mmol) and TBTU (92 mg, 0.29 mmol) in 2 mL ACN was treated with DIEA (117 μL, 0.84 mmol) and stirred overnight. The reaction was poured into dilute aq. Na$_2$CO$_3$ solution and extracted with DCM. The combined extracts were passed through a phase separator and concentrated. The crude product was used in the next step without further purification. (m/z=679.6 [M+H], RT=1.32 min (HPLC-Method C)).

To a solution of the above mentioned product (141 mg, 0.21 mmol) in 2 mL dioxane was added 1 mL of 4M HCl in dioxane solution and the reaction was stirred overnight. The reaction was concentrated to dryness under a stream of nitrogen and the residue was used in the next step without further purification.

To the above mentioned product in 2 mL of THF was added TBAF (1M in THF, 95 μL, 0.095 mmol) and the reaction was stirred over night. The reaction was concentrated to dryness, taken up in 2 mL DMF, filtered and purified by RHPLC to give *Ex 43 (14 mg, 0.04 mmol, 16% over three steps).

*The stereochemistry at the 3-position of the pyrrolidine-ring of the enantiomerically pure compound was not determined.

Therapeutic Use

On the basis of their biological properties the compounds of formula (I) according to the invention, or their tautomers, racemates, enantiomers, diastereomers, mixtures thereof and the salts of all the above-mentioned forms are suitable for treating inflammatory disorders and disorders of epithelial barrier tissues, in that they exhibit good inhibitory effect upon Vanin-1.

Such diseases include for example: Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, colorectal cancer and pancreatic cancer related new onset diabetes.

The compounds of formula (I) may be used on their own or in combination with at least one other active substance according to the invention, and/or optionally also in combination with at least one other pharmacologically active substance. The other pharmacologically active substance may be an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists and methotrexate. Suitable preparations for administering the compounds of formula 1 will be apparent to those with ordinary skill in the art and include for example tablets, pills, capsules, suppositories, lozenges, troches, solutions, syrups, elixirs, sachets, injectables, inhalatives and powders etc. Suitable tablets may be obtained, for example, by mixing one or more compounds according to formula I with known excipients, for example inert diluents, carriers, disintegrants, adjuvants, surfactants, binders and/or lubricants.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

Description of Biological Properties

Vanin-1 Enzymatic Assay:

The test compounds are dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions are prepared, a further intermediate dilutions of the substances is carried out with assay buffer resulting in 1% final DMSO concentration in the assay.

Method 1): 0.15 nM of FLAG-tagged Vanin-1 (AA 22-493, T26I, produced internally) and test compounds are incubated at room temperature for 15 minutes in assay buffer (1 mM DTT, 0.0025% Brij-35, 50 mM HEPES, pH7.5). 3 µM D-Pantethine (Sigma, Cat#P2125-5G) in assay buffer is added and incubated for additional 30 minutes at room temperature. Reaction is stopped by adding equal volume of stop solution as the reaction mixture to reach 5 nM Nevirapine (as an internal standard) and 0.5% TFA. Assay plates are centrifuged for 2 minutes and the formation of pantothenic acid is detected by RapidFire Mass Spectrometry (mobile phase A: 0.1% formic acid in water, mobile phase B: 100% methanol) using graphitic carbon cartridge (Agilent Cat #G9206A).

Method 2): 0.1 nM of FLAG-tagged Vanin-1 (AA 22-493, T26I, produced internally) and test compounds are incubated at room temperature for 20 minutes in assay buffer (1 mM DTT, 0.0025% Brij-35, 50 mM HEPES, pH7.5). D-Pantethine (Sigma, Cat#P2125-5G) in assay buffer is added (final concentration 3 µM) and incubated for additional 30 minutes at room temperature. Total assay volume typically is 40 µl but might be adjusted according to needs. Reaction is stopped by adding equal volume of stop solution as the reaction mixture to reach 100 nM HD-pantothenic acid (as an internal standard) and 1% TFA. Assay plates are centrifuged for 2 minutes and the formation of pantothenic acid is detected by RapidFire Mass Spectrometry (mobile phase A: 0.1% formic acid and 0.01% trifluoroacetic acid in water; mobile phase B: 47.5% acetonitrile, 47.5% methanol, 0.1% formic acid and 0.01% trifluoroacetic acid in water) using a C18, 12 µL cartridge (Agilent Cat #G9205A).

Please see Table I for results.

The values given in Table I result from measurements of one or more samples. In case of multiple measurements the geometric mean values determined by method 1 and/or method 2 are given.

Human Whole Blood Assay:

250 µl human whole blood and 7 µl pre-diluted compound in RPMI 1640 media are incubated at room temperature for 15 minutes on an orbital shaker. 10 µl of D-Pantethine (Sigma, Cat#P2125-5G) is added, resulting in 10 µM final concentration, for additional 30 minutes incubation at room temperature. The reaction is stopped by placed on ice for 5 minutes. Assay plates are centrifuged at 1800 rpm at 4° C. for 10 minutes. 80 µl of plasma is mixed with 80 µl of ice-cold acetonitrile and is left on ice for 5 minutes. The reaction mixture is centrifuged at 4000 rpm for 10 min at 4° C. 50 µl of the supernatant is mixed with 150 µl of ice-cold $H_2O$. The above solution is mixed with equal volume of stop solution to reach 5 nM Nevirapine (as an internal standard) and 0.4% TFA. The mixture is centrifuged at 4000 rpm for 10 minutes. The formation of pantothenic acid is detected by RapidFire Mass Spectrometry (mobile phase A: 0.1% Formic acid in water, mobile phase B: 100% Methanol) using graphitic carbon cartridge (Agilent Cat #G9206A). Please see Table I for results. The values given in Table I result from measurements of one or more samples. In case of multiple measurements the geometric mean values are given.

Other features and advantages of the present invention will become apparent from the following more detailed Examples which illustrate, by way of example, the principles of the invention TABLE I
Biological and physical properties of representatives of the present invention
| Ex. | Structure | VNN 1 IC$_{50}$ (nM) | VNN1- assay method(s) | HWB IC$_{50}$ (nM) | HPLC Method | RT (min) | m/z [M + H]$^+$ or [M]+ |
|---|---|---|---|---|---|---|---|
| 1 | 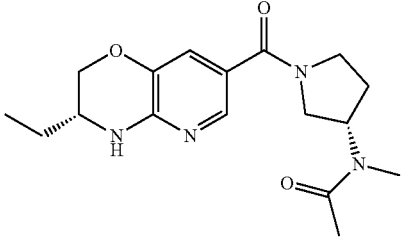 [SMILES: CC[C@@H]1COc2cc(C(=O)N3CC[C@H](N(C)C(C)=O)C3)cnc2N1] | 3.3 | 1 + 2 | 20 | B | 2.24 | 333.2 |
| 2 | 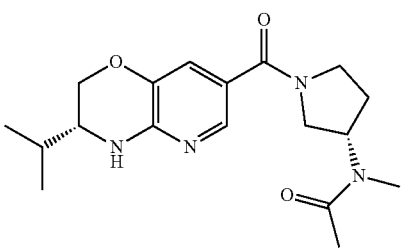 [SMILES: CC(=O)N(C)[C@H]1CCN(C(=O)c2cnc3c(c2)OC[C@@H](C(C)C)N3)C1] | 3.6 | 1 | 26 | B | 2.4 | 347.3 |
| 3 | 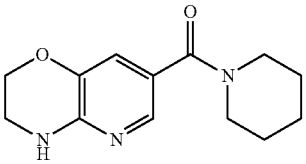 [SMILES: O=C(c1cnc2c(c1)OCCN2)N1CCCCC1] | 2800 | 1 + 2 | | B | 1.55 | 249.1 |
| 4 | 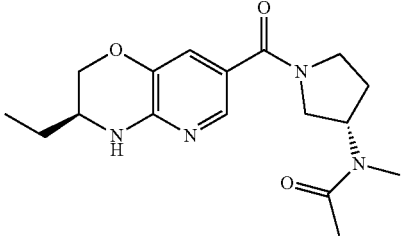 [SMILES: CC[C@H]1COc2cc(C(=O)N3CC[C@H](N(C)C(C)=O)C3)cnc2N1] | 1.3 | 1 | 22 | B | 2.24 | 333.2 |
| 5 | 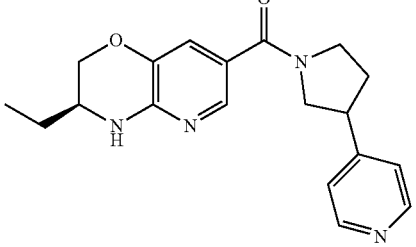 | 3.1 | 1 + 2 | 76 | B | 1.98 | 339 |
| 6 | 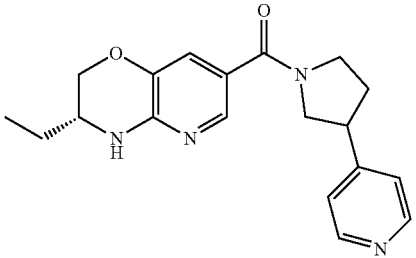 [SMILES: CC[C@@H]1COc2cc(C(=O)N3CCC(c4ccncc4)C3)cnc2N1] | 8.9 | 1 | 99 | B | 1.98 | 339 |

TABLE I-continued

Biological and physical properties of representatives of the present invention

| Ex. | Structure | VNN1 IC$_{50}$ (nM) | VNN1-assay method(s) | HWB IC$_{50}$ (nM) | HPLC Method | RT (min) | m/z [M + H]$^+$ or [M]+ |
|---|---|---|---|---|---|---|---|
| 7 | 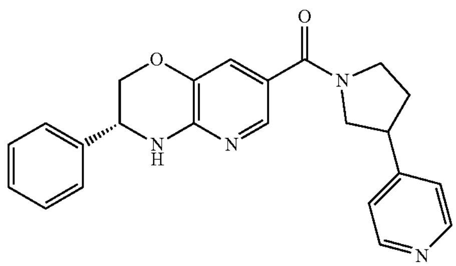 [SMILES: O=C(c1cnc2c(c1)OC[C@@H](c1ccccc1)N2)N1CCC(c2ccncc2)C1] | 6200 | 1 | | B | 2.36 | 387 |
| 8 | 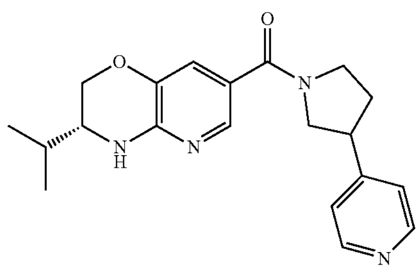 [SMILES: CC(C)[C@@H]1COc2cc(C(=O)N3CCC(c4ccncc4)C3)cnc2N1] | 17.2 | 1 | | B | 2.14 | 353.1 |
| 9 | 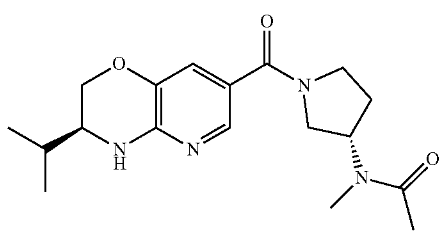 [SMILES: CC(=O)N(C)[C@H]1CCN(C(=O)c2cnc3c(c2)OC[C@H](C(C)C)N3)C1] | 1.5 | 1 | 23 | B | 2.41 | 346.8 |
| 10 | 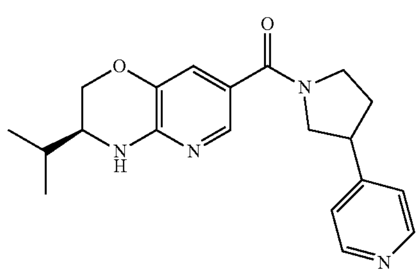 [SMILES: CC(C)[C@H]1COc2cc(C(=O)N3CCC(c4ccncc4)C3)cnc2N1] | 2.4 | 1 | 146 | B | 2.15 | 353.1 |
| *11 | 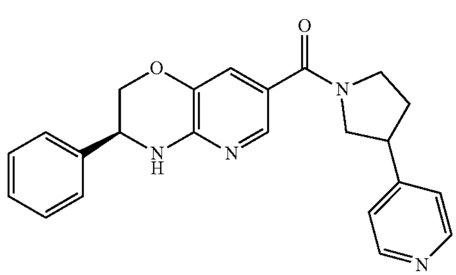 [SMILES: O=C(c1cnc2c(c1)OC[C@H](c1ccccc1)N2)N1CCC(c2ccncc2)C1] | 19.0 | 1 | 3700 | D | 1.38 | 387.1 |

TABLE I-continued

Biological and physical properties of representatives of the present invention

| Ex. | Structure | VNN 1 IC$_{50}$ (nM) | VNN1-assay method(s) | HWB IC$_{50}$ (nM) | HPLC Method | RT (min) | m/z [M + H]$^+$ or [M]+ |
|---|---|---|---|---|---|---|---|
| *12 | 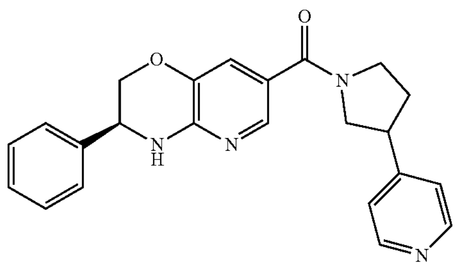 [SMILES: O=C(c1cnc2c(c1)OC[C@H](c1ccccc1)N2)N1CCC(c2ccncc2)C1] | 1.8 | 1 | 330 | D | 1.38 | 387.1 |
| 13 | 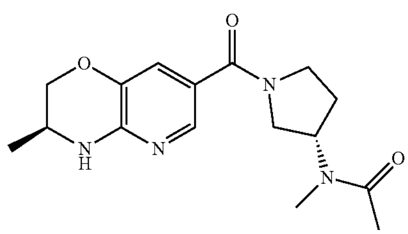 [SMILES: CC(=O)N(C)[C@H]1CCN(C(=O)c2cnc3c(c2)OC[C@H](C)N3)C1] | 1.8 | 1 + 2 | 23 | A | 0.52 | 319 |
| 14 | 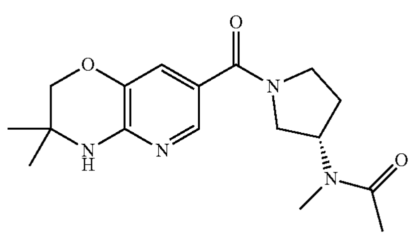 [SMILES: CC(=O)N(C)[C@H]1CCN(C(=O)c2cnc3c(c2)OCC(C)(C)N3)C1] | 0.5 | 1 + 2 | 12 | A | 0.88 | 334.2 |
| 15 | 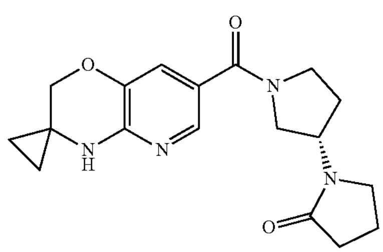 [SMILES: O=C(c1cnc2c(c1)OCC1(CC1)N2)N1CC[C@H](N2CCCC2=O)C1] | 0.7 | 2 | 7.8 | D | 0.86 | 343.5 |
| 16 | 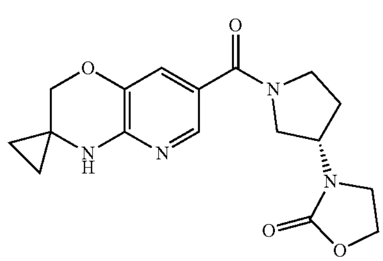 [SMILES: O=C(c1cnc2c(c1)OCC1(CC1)N2)N1CC[C@H](N2CCOC2=O)C1] | 0.6 | 2 | 8.9 | D | 0.77 | 345.4 |

TABLE I-continued

Biological and physical properties of representatives of the present invention

| Ex. | Structure | VNN 1 IC$_{50}$ (nM) | VNN1-assay method(s) | HWB IC$_{50}$ (nM) | HPLC Method | RT (min) | m/z [M + H]$^+$ or [M]+ |
|---|---|---|---|---|---|---|---|
| 17 | 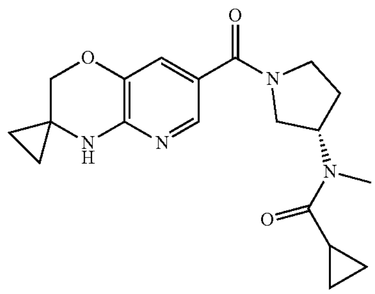 [SMILES: CN(C(=O)C1CC1)[C@H]1CCN(C(=O)c2cnc3c(c2)OCC2(CC2)N3)C1] | 0.7 | 2 | 8.8 | D | 1.11 | 357.4 |
| 18 | 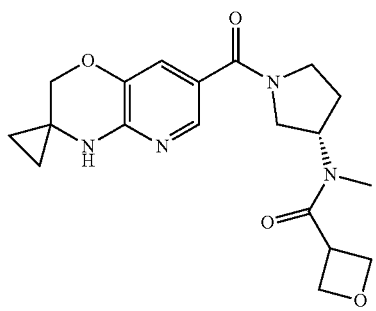 [SMILES: CN(C(=O)C1COC1)[C@H]1CCN(C(=O)c2cnc3c(c2)OCC2(CC2)N3)C1] | 0.9 | 2 | 12 | C | 0.36 | 373.4 |
| 19 | 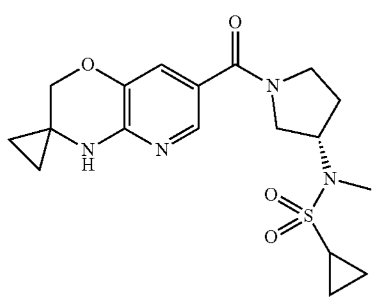 [SMILES: CN([C@H]1CCN(C(=O)c2cnc3c(c2)OCC2(CC2)N3)C1)S(=O)(=O)C1CC1] | 2.3 | 2 | 39 | C | 0.61 | 393.4 |
| *20 | 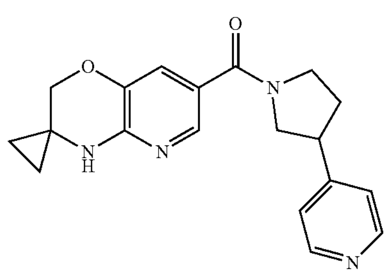 [SMILES: O=C(c1cnc2c(c1)OCC1(CC1)N2)N1CCC(c2ccncc2)C1] | 1.9 | 1 | 130 | A | 0.66 | 336.9 |
| 21 | 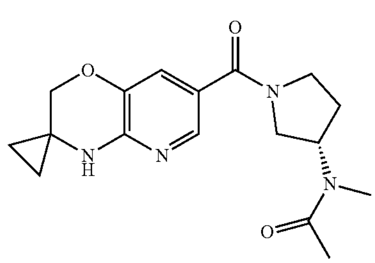 [SMILES: CC(=O)N(C)[C@H]1CCN(C(=O)c2cnc3c(c2)OCC2(CC2)N3)C1] | 0.4 | 1 + 2 | 10 | A | 0.67 | 331.4 |

TABLE I-continued

Biological and physical properties of representatives of the present invention

| Ex. | Structure | VNN 1 IC$_{50}$ (nM) | VNN1- assay method(s) | HWB IC$_{50}$ (nM) | HPLC Method | RT (min) | m/z [M + H]+ or [M]+ |
|---|---|---|---|---|---|---|---|
| *22 | 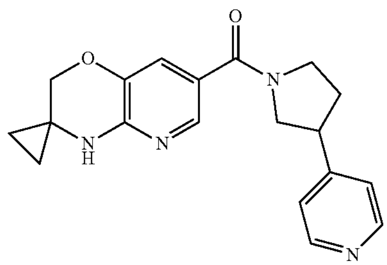 [SMILES: O=C(c1cnc2c(c1)OCC1(CC1)N2)N1CCC(c2ccncc2)C1] | 0.4 | 1 | 37 | A | 0.66 | 336.9 |
| 23 | 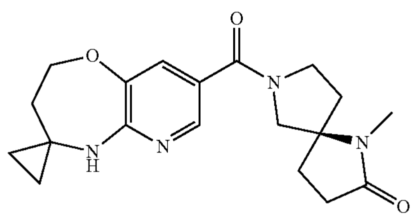 [SMILES: CN1C(=O)CC[C@]12CCN(C(=O)c1cnc3c(c1)OCCC1(CC1)N3)C2] | 8.1 | 2 | 50 | A | 0.60 | 357 |
| 24 | 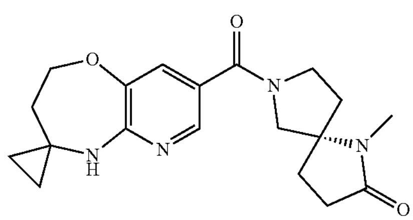 [SMILES: CN1C(=O)CC[C@@]12CCN(C(=O)c1cnc3c(c1)OCCC1(CC1)N3)C2] | 0.6 | 2 | 6.5 | A | 0.60 | 357 |
| 25 | 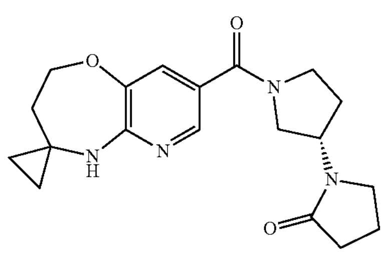 [SMILES: O=C(c1cnc2c(c1)OCCC1(CC1)N2)N1CC[C@H](N2CCCC2=O)C1] | 0.1 | 2 | 3.1 | A | 0.61 | 357 |
| 26 | 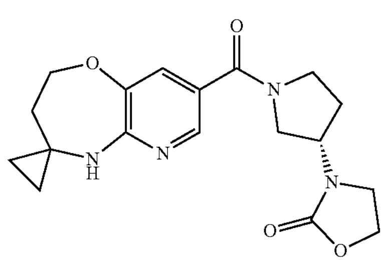 [SMILES: O=C(c1cnc2c(c1)OCCC1(CC1)N2)N1CC[C@H](N2CCOC2=O)C1] | 0.2 | 2 | 5.9 | A | 0.59 | 359 |
| 27 | 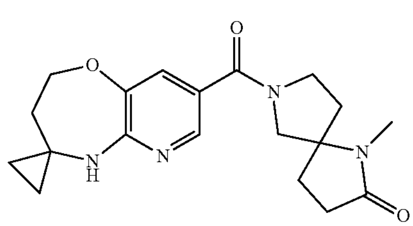 [SMILES: CN1C(=O)CCC12CCN(C(=O)c1cnc3c(c1)OCCC1(CC1)N3)C2] | 1.09 | 2 | 11 | A | 0.6 | 357 |

TABLE I-continued

Biological and physical properties of representatives of the present invention

| Ex. | Structure | VNN 1 IC$_{50}$ (nM) | VNN1- assay method(s) | HWB IC$_{50}$ (nM) | HPLC Method | RT (min) | m/z [M + H]$^+$ or [M]+ |
|---|---|---|---|---|---|---|---|
| 28 | 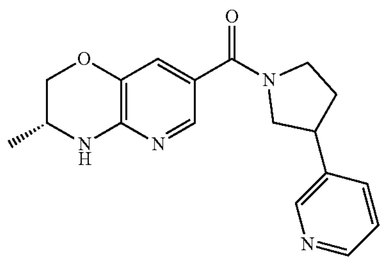 [SMILES: C[C@@H]1COc2cc(C(=O)N3CCC(c4cccnc4)C3)cnc2N1] | 3.8 | 1 | 168 | A | 0.64 | 324.9 |
| 29 | 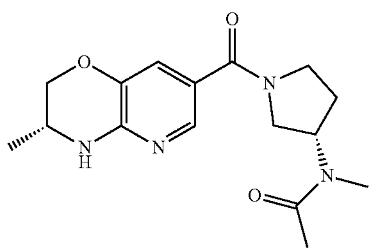 | 3.3 | 1 + 2 | 28 | A | 0.52 | 318.9 |
| 30 | 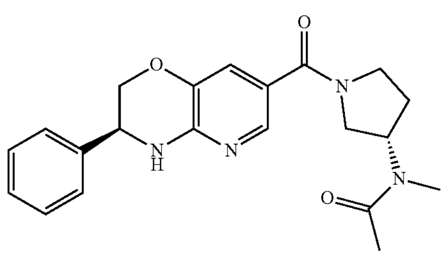 [SMILES: CC(=O)N(C)[C@H]1CCN(C(=O)c2cnc3c(c2)OC[C@H](c2ccccc2)N3)C1] | 2.4 | 1 + 2 | 43 | B | 2.89 | 381 |
| 31 | 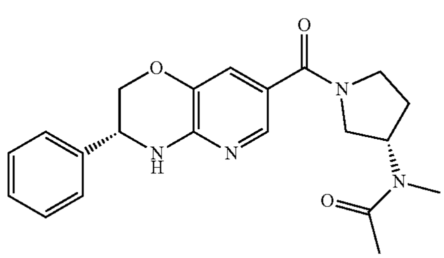 [SMILES: CC(=O)N(C)[C@H]1CCN(C(=O)c2cnc3c(c2)OC[C@@H](c2ccccc2)N3)C1] | 1747.3 | 1 + 2 | | B | 2.71 | 380.8 |
| 32 | 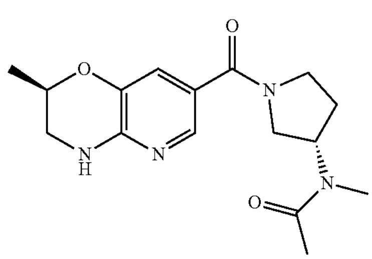 | 1.3 | 1 | 14 | B | 2.06 | 319.9 |

… 75 … 76
TABLE I-continued
Biological and physical properties of representatives of the present invention
| Ex. | Structure | VNN 1 IC$_{50}$ (nM) | VNN1-assay method(s) | HWB IC$_{50}$ (nM) | HPLC Method | RT (min) | m/z [M + H]$^+$ or [M]+ |
|---|---|---|---|---|---|---|---|
| 33 | 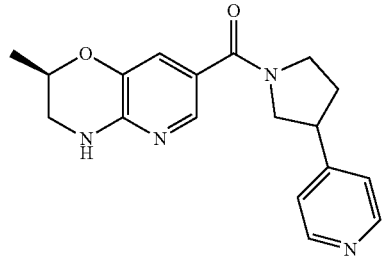 [SMILES: C[C@@H]1CNc2ncc(C(=O)N3CCC(c4ccncc4)C3)cc2O1] | 2.5 | 1 | 34 | B | 1.5 | 325 |
| 34 | 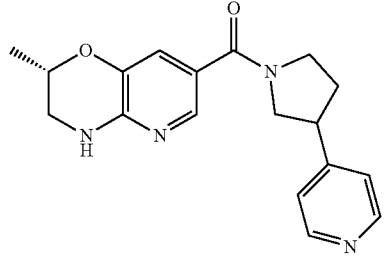 [SMILES: C[C@H]1CNc2ncc(C(=O)N3CCC(c4ccncc4)C3)cc2O1] | 3.5 | 1 + 2 | 44 | B | 2.03 | 325.3 |
| 35 | 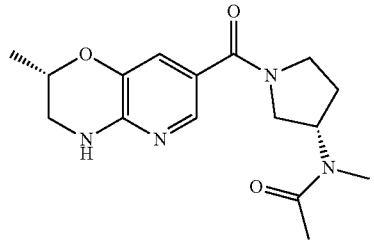 | 26.1 | 1 + 2 | 190 | B | 2.06 | 319.2 |
| 37 | 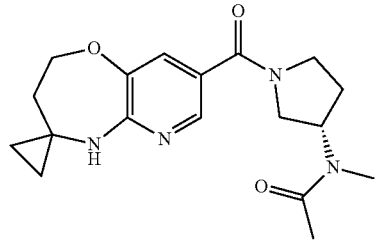 [SMILES: CC(=O)N(C)[C@H]1CCN(C(=O)c2cnc3c(c2)OCCC2(CC2)N3)C1] | 0.2 | 1 + 2 | 6.3 | A | 0.62 | 345 |
| *38 | 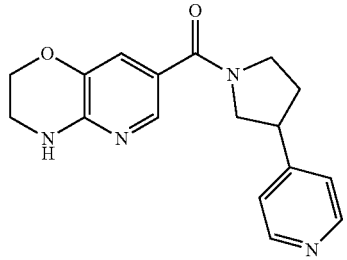 [SMILES: O=C(c1cnc2c(c1)OCCN2)N1CCC(c2ccncc2)C1] | 14.2 | 1 + 2 | 210 | C | 0.57 | 310.4 |

TABLE I-continued

Biological and physical properties of representatives of the present invention

| Ex. | Structure | VNN 1 IC$_{50}$ (nM) | VNN1- assay method(s) | HWB IC$_{50}$ (nM) | HPLC Method | RT (min) | m/z [M + H]$^+$ or [M]+ |
|---|---|---|---|---|---|---|---|
| 39 | 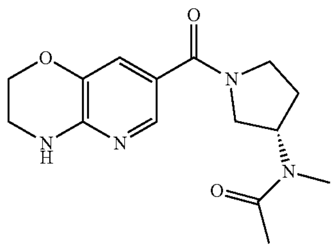 [SMILES: CC(=O)N(C)[C@H]1CCN(C(=O)c2cnc3c(c2)OCCN3)C1] | 8.1 | 1 + 2 | 120 | C | 0.46 | 304.3 |
| 40 | 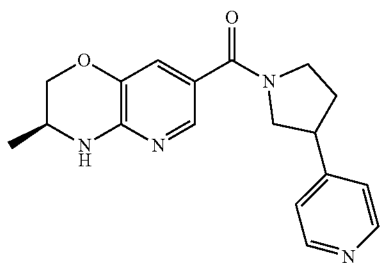 [SMILES: C[C@H]1COc2cc(C(=O)N3CCC(c4ccncc4)C3)cnc2N1] | 1.7 | 1 + 2 | 87 | A | 0.64 | 325 |
| 41 | 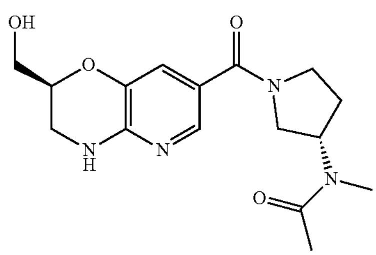 [SMILES: CC(=O)N(C)[C@H]1CCN(C(=O)c2cnc3c(c2)O[C@H](CO)CN3)C1] | 2.5 | 1 + 2 | 18 | A | 0.41 | 334.4 |
| 42 | 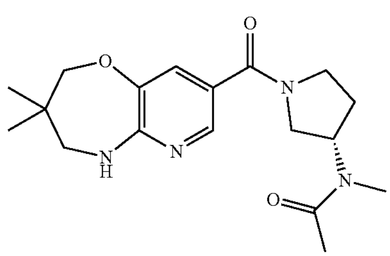 | 1.1 | 1 + 2 | 16 | A | 0.68 | 347 |
| *43 | 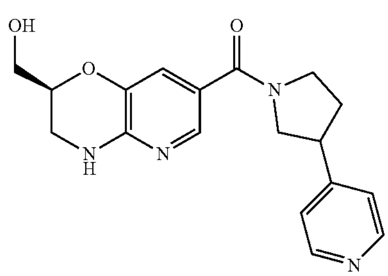 [SMILES: O=C(c1cnc2c(c1)O[C@H](CO)CN2)N1CCC(c2ccncc2)C1] | 3.7 | 1 | 66 | A | 0.52 | 340.4 |

TABLE I-continued

Biological and physical properties of representatives of the present invention

| Ex. | Structure | VNN 1 IC$_{50}$ (nM) | VNN1- assay method(s) | HWB IC$_{50}$ (nM) | HPLC Method | RT (min) | m/z [M + H]$^+$ or [M]+ |
|---|---|---|---|---|---|---|---|
| 44 | 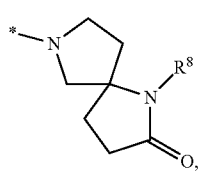 | 1.7 | 1 + 2 | 23 | A | 0.53 | 318 |

*The stereochemistry at the 3-position of the pyrrolidine-ring of the enantiomerically pure compound was not determined.

The invention claimed is:

1. A compound of the formula (I),

(I)

wherein
A is a group of formula A.1 or A.2:

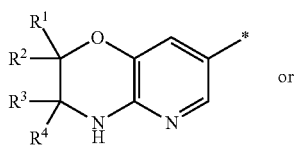
A.1 or

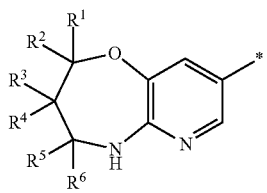
A.2 wherein each R$^1$, R$^2$, R$^3$, R$^4$, R$^5$ and R$^6$ is independently selected from the group consisting of H, C$_{1-4}$-alkyl, C$_{1-4}$-alkyl substituted with a hydroxyl or halogen group, phenyl and a 5-6 membered heteroaryl, or
R$^1$ and R$^2$, R$^3$ and R$^4$, or R$^5$ and R$^6$ together form a 3-4 membered carbocycle, and
wherein
B is selected from the group consisting of formulas B.1, B.2 and B.3:

B.1

B.2

B.3 wherein
R$^7$ is H, C$_{1-3}$-alkyl, halogen, C$_{1-3}$-alkoxy, 5-6 membered heteroaryl, or
R$^7$ is selected from the group consisting of R$^{7.a}$, R$^{7.b}$ and R$^{7.c}$

R$^{7.a}$

R$^{7.b}$

R$^{7.c}$ wherein
R$^8$ is selected from the group consisting of C$_{1-6}$-alkyl, C$_{3-6}$-cycloalkyl, and 3-14 membered heterocyclyl and
X is CH$_2$ or O;
or a pharmaceutically acceptable salt thereof.

2. The compound according to claim 1, wherein
A is selected from the group consisting of formulas A.1a to A.1f

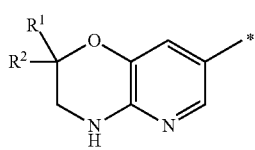
A.1a

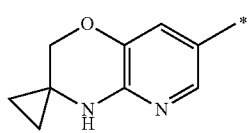
A.1b

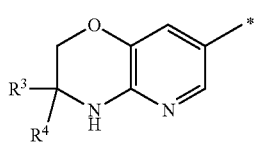
A.1c

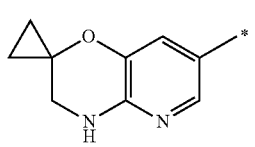
A.1d

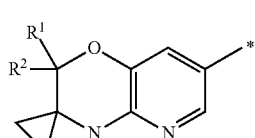
A.1e

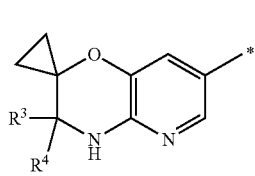
A.1f or a pharmaceutically acceptable salt thereof.

3. The compound according to claim 1, wherein A is selected from the group consisting of formulas A.2a to A.2g

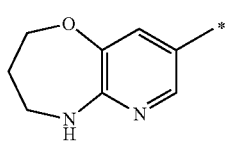
A.2a

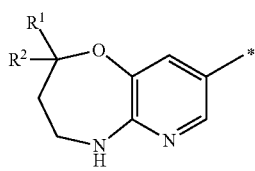
A.2b

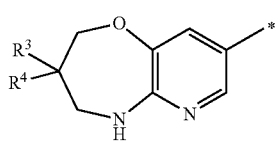
A.2c

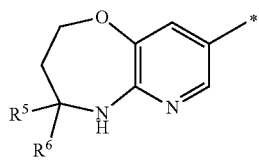
A.2d

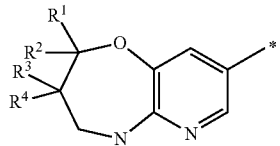
A.2e

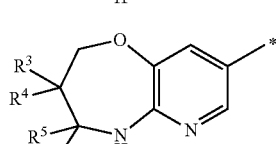
A.2f

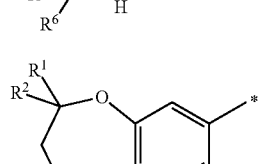
A.2g or a pharmaceutically acceptable salt thereof.

4. The compound according to claim 1, wherein B denotes B.1 or B.2

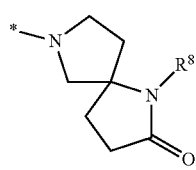
B.1

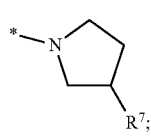
B.2 or a pharmaceutically acceptable salt thereof.

5. The compound according to claim 1, wherein B denotes B.2

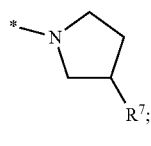
B.2 or a pharmaceutically acceptable salt thereof.

6. The compound according to claim 1, wherein each $R^1$ and $R^2$ is independently selected from the group consisting of H, $CH_3$ and —$CH_2OH$, or a pharmaceutically acceptable salt thereof.

7. The compound according to claim 1, wherein
R¹ and R² together form a 3-4 membered carbocycle;
or a pharmaceutically acceptable salt thereof.

8. The compound according to claim 1, wherein each $R^3$ and $R^4$ is independently selected from the group consisting of H, $C_{1-3}$-alkyl and phenyl;
or a pharmaceutically acceptable salt thereof.

9. The compound according to claim 1, wherein
$R^3$ and $R^4$ together form a 3-4 membered carbocycle;
or a pharmaceutically acceptable salt thereof.

10. The compound according to claim 1, wherein
$R^5$ and $R^6$ denote H or
$R^5$ and $R^6$ together form a 3-4 membered carbocycle;
or a pharmaceutically acceptable salt thereof.

11. The compound according to claim 1, wherein
$R^7$ is 5-6 membered heteroaryl or
$R^7$ is selected from the group consisting of formulas $R^{7.a}$, $R^{7.b}$ and $R^{7.c}$;

$R^{7.a}$ $R^{7.b}$ $R^{7.c}$ or a pharmaceutically acceptable salt thereof.

12. The compound according to claim 1, wherein
$R^8$ is selected from the group consisting of $C_{1-3}$-alkyl, $C_{3-6}$-cycloalkyl and 3-6 membered heterocyclyl;
or a pharmaceutically acceptable salt thereof.

13. The compound according to claim 1, wherein
X is $CH_2$ or O;
or a pharmaceutically acceptable salt thereof.

14. The compound of formula I, according to claim 1 selected from the group consisting of examples 14, 15, 16, 17, 21, 22, 25, 26, 37 and 42 listed below:

Ex. 14

-continued

Ex.15

Ex. 16

Ex.17

Ex.21

Ex.22

Ex.25

-continued

Ex.26
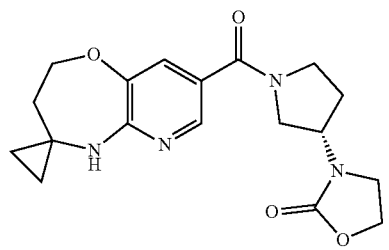

Ex.37
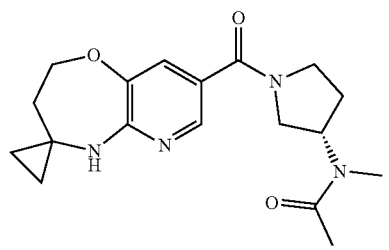

Ex.42
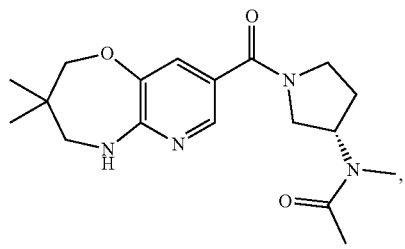

or a pharmaceutically acceptable salt thereof.

15. A pharmaceutical composition comprising a therapeutically effective amount of at least one compound of formula I according to claim 1 or a pharmaceutically acceptable salt thereof and one or more pharmaceutically acceptable excipients.

16. A method of treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, colorectal cancer or pancreatic cancer related new onset diabetes, comprising administering to the patient a therapeutically effective amount of a compound according to claim 1.

17. A method of treating a patient suffering from Crohn's disease, comprising administering to the patient a therapeutically effective amount of a compound according to claim 1.

18. A method of treating a patient suffering from atopic dermatitis, comprising administering to the patient a therapeutically effective amount of a compound according to claim 1.

19. A method of treating a patient suffering from ulcerative colitis, comprising administering to the patient a therapeutically effective amount of a compound according to claim 1.

20. A compound of formula:

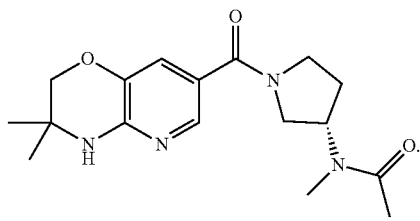 [SMILES: CC(=O)N(C)[C@H]1CCN(C(=O)c2cnc3c(c2)OCC(C)(C)N3)C1]

21. A compound of formula:

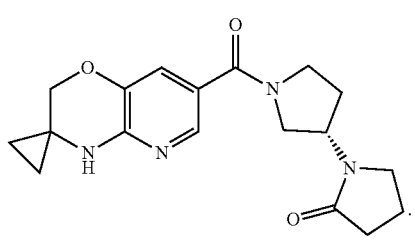 [SMILES: O=C(c1cnc2c(c1)OCC1(CC1)N2)N1CC[C@H](N2CCCC2=O)C1]

22. A compound of formula:

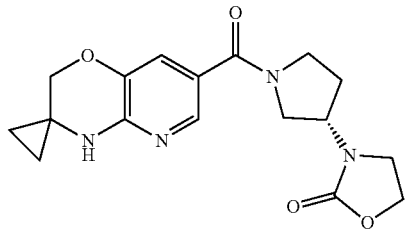 [SMILES: O=C(c1cnc2c(c1)OCC1(CC1)N2)N1CC[C@H](N2CCOC2=O)C1]

23. A compound of formula:

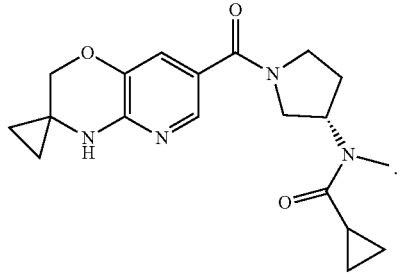 [SMILES: CN(C(=O)C1CC1)[C@H]1CCN(C(=O)c2cnc3c(c2)OCC2(CC2)N3)C1]

24. A compound of formula:

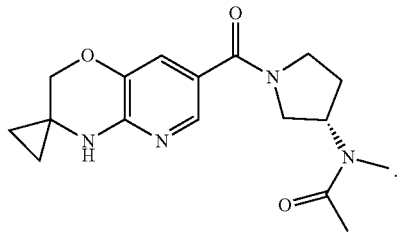 [SMILES: CC(=O)N(C)[C@H]1CCN(C(=O)c2cnc3c(c2)OCC2(CC2)N3)C1]

25. A compound of formula:

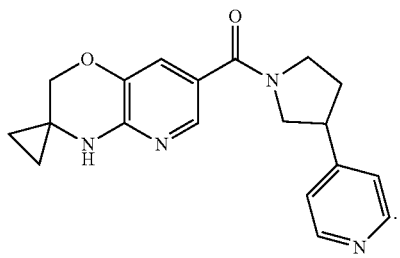 [SMILES: O=C(c1cnc2c(c1)OCC1(CC1)N2)N1CCC(c2ccncc2)C1]

26. A compound of formula:

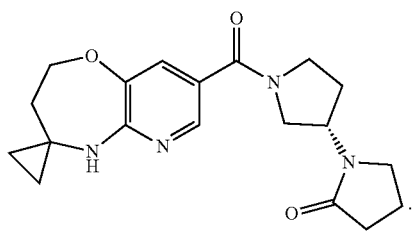 [SMILES: O=C(c1cnc2c(c1)OCCC1(CC1)N2)N1CC[C@H](N2CCCC2=O)C1]

27. A compound of formula:

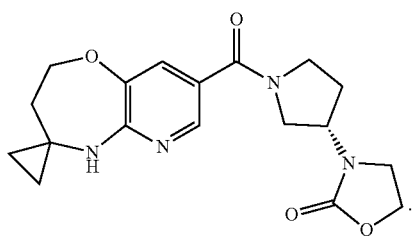 [SMILES: O=C(c1cnc2c(c1)OCCC1(CC1)N2)N1CC[C@H](N2CCOC2=O)C1]

28. A compound of formula:

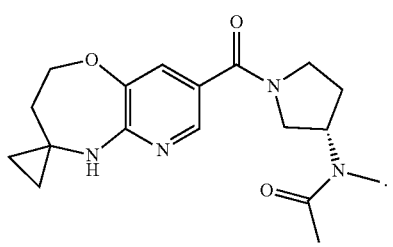 [SMILES: CC(=O)N(C)[C@H]1CCN(C(=O)c2cnc3c(c2)OCCC2(CC2)N3)C1]

29. A compound of formula:

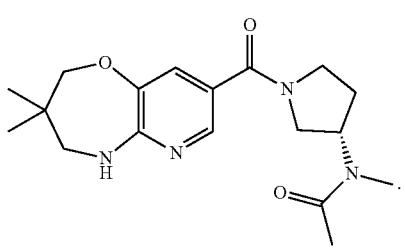

30. A compound of formula:

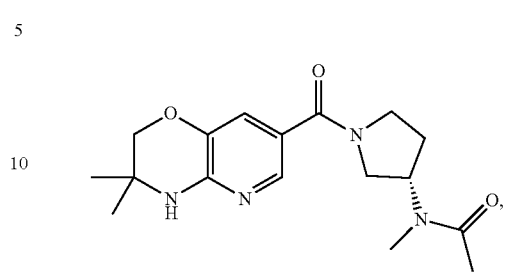

or a pharmaceutically acceptable salt thereof.

31. A compound of formula:

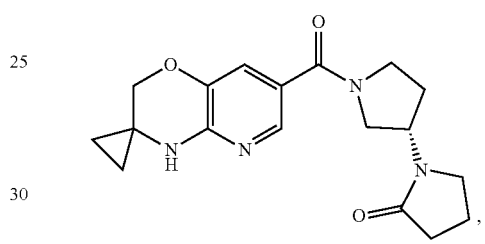

pharmaceutically acceptable salt thereof.

32. A compound of formula:

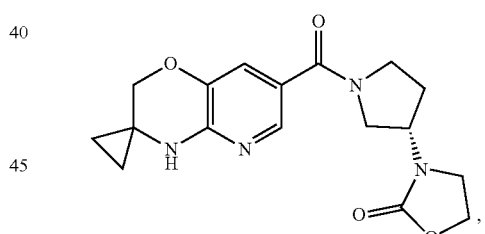

pharmaceutically acceptable salt thereof.

33. A compound of formula:

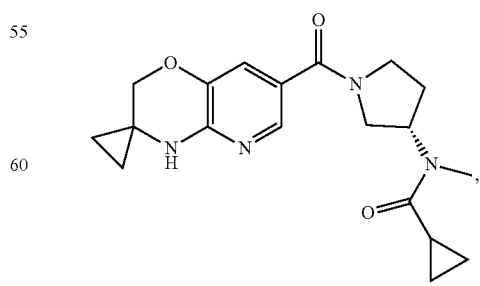

pharmaceutically acceptable salt thereof.

34. A compound of formula:

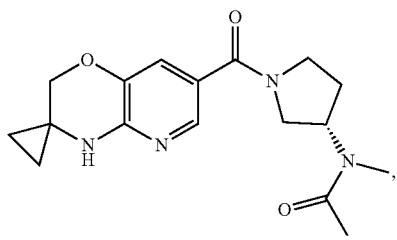 [SMILES: CC(=O)N(C)[C@H]1CCN(C(=O)c2cnc3c(c2)OCC2(CC2)N3)C1]

pharmaceutically acceptable salt thereof.

35. compound of formula:

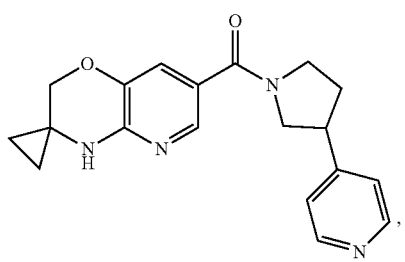 [SMILES: O=C(c1cnc2c(c1)OCC1(CC1)N2)N1CCC(c2ccncc2)C1]

pharmaceutically acceptable salt thereof.

36. A compound of formula:

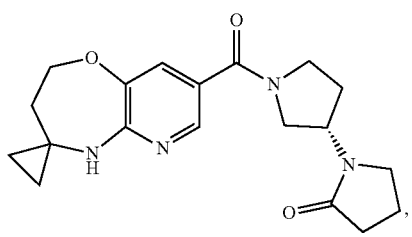 [SMILES: O=C(c1cnc2c(c1)OCCC1(CC1)N2)N1CC[C@H](N2CCCC2=O)C1]

pharmaceutically acceptable salt thereof.

37. A compound of formula:

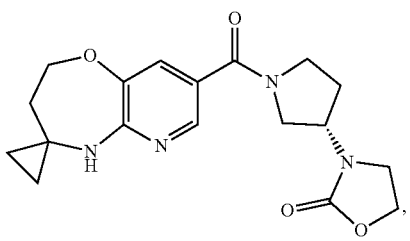 [SMILES: O=C(c1cnc2c(c1)OCCC1(CC1)N2)N1CC[C@H](N2CCOC2=O)C1]

pharmaceutically acceptable salt thereof.

38. A compound of formula:

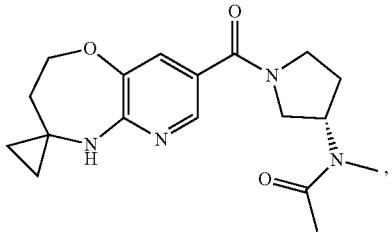 [SMILES: CC(=O)N(C)[C@H]1CCN(C(=O)c2cnc3c(c2)OCCC2(CC2)N3)C1]

pharmaceutically acceptable salt thereof.

39. A compound of formula:

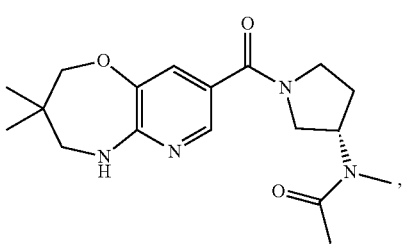

pharmaceutically acceptable salt thereof.

* * * * *

UNITED STATES PATENT AND TRADEMARK OFFICE
CERTIFICATE OF CORRECTION

PATENT NO. : 10,364,255 B2
APPLICATION NO. : 16/003252
DATED : July 30, 2019
INVENTOR(S) : Todd Bosanac et al.

It is certified that error appears in the above-identified patent and that said Letters Patent is hereby corrected as shown below:

In the Claims

In Column 88, Claim 31, the portion reading "pharmaceutically acceptable salt thereof" at Line 34 should read --or a pharmaceutically acceptable salt thereof--.

In Column 88, Claim 32, the portion reading "pharmaceutically acceptable salt thereof" at Line 50 should read --or a pharmaceutically acceptable salt thereof--.

In Column 88, Claim 33, the portion reading "pharmaceutically acceptable salt thereof" at Line 67 should read --or a pharmaceutically acceptable salt thereof--.

In Column 89, Claim 34, the portion reading "pharmaceutically acceptable salt thereof" at Line 14 should read --or a pharmaceutically acceptable salt thereof--.

In Column 89, Claim 35, the portion reading "pharmaceutically acceptable salt thereof" at Line 30 should read --or a pharmaceutically acceptable salt thereof--.

In Column 89, Claim 36, the portion reading "pharmaceutically acceptable salt thereof" at Line 50 should read --or a pharmaceutically acceptable salt thereof--.

In Column 90, Claim 37, the portion reading "pharmaceutically acceptable salt thereof" at Line 14 should read --or a pharmaceutically acceptable salt thereof--.

In Column 90, Claim 38, the portion reading "pharmaceutically acceptable salt thereof" at Line 28 should read --or a pharmaceutically acceptable salt thereof--.

In Column 90, Claim 39, the portion reading "pharmaceutically acceptable salt thereof" at Line 44 should read --or a pharmaceutically acceptable salt thereof--.

Signed and Sealed this
Twenty-first Day of April, 2020

Andrei Iancu
*Director of the United States Patent and Trademark Office*